United States Patent
Dugar et al.

(10) Patent No.: US 9,428,482 B2
(45) Date of Patent: Aug. 30, 2016

(54) PROCESS FOR SYNTHESIS OF POLYPHENOLS

(75) Inventors: Sundeep Dugar, San Jose, CA (US); Dinesh Mahajan, Haryana (IN); Peter Giannousis Pantelis, Pacifica, CA (US); Vijay Singh, Himachal Pradesh (IN); Kamal Kishore Kapoor, Jammu (IN)

(73) Assignee: SPHAERA PHARMA PTE. LTD., Singapore (SG)

( * ) Notice: Subject to any disclaimer, the term of this patent is extended or adjusted under 35 U.S.C. 154(b) by 91 days.

(21) Appl. No.: 13/981,279

(22) PCT Filed: Jan. 24, 2012

(86) PCT No.: PCT/IN2012/000052
§ 371 (c)(1),
(2), (4) Date: Oct. 7, 2013

(87) PCT Pub. No.: WO2012/101652
PCT Pub. Date: Aug. 2, 2012

(65) Prior Publication Data
US 2014/0031421 A1    Jan. 30, 2014

(30) Foreign Application Priority Data
Jan. 27, 2011   (IN) .............................. 196/DEL/2011

(51) Int. Cl.
*C07D 311/74*    (2006.01)
*C07D 311/30*    (2006.01)

(52) U.S. Cl.
CPC ............ *C07D 311/74* (2013.01); *C07D 311/30* (2013.01)

(58) Field of Classification Search
CPC ..................................................... C07D 311/74
See application file for complete search history.

(56) References Cited

U.S. PATENT DOCUMENTS

| | | | |
|---|---|---|---|
| 4,644,011 A | 2/1987 | Ballenegger et al. | |
| 6,476,241 B1 | 11/2002 | Kozikowski et al. | |
| 2006/0234957 A1 | 10/2006 | Tsuda et al. | |
| 2010/0048920 A1 | 2/2010 | Romanczyk, Jr. et al. | |

FOREIGN PATENT DOCUMENTS

EP         0445819 A2  *  9/1991
WO   WO 2008153945 A2  * 12/2008

OTHER PUBLICATIONS

Waiss, A.C., et al. "Synthesis of flav-2-enes and flav-3-enes." Chemistry & Industry. Jun. 8, 1968, pp. 743-744.*
"Phytochemicals: Epicatechin." © 2014.*
Cayman Chemicals. "(−)-Epigallocatechin gallate." © 2014.*
Nogradi, et al. Product class 2: benzopyrylium salts. Science of Synthesis. (2003), vol. 14, pp. 201-273.*
Bergot, B.J., et al. "Anthocyanins and Related Compounds: V. Formation of Bisflavenylidenes From Flavones by Reductive Dimerization." Tetrahedron. (1965), vol. 21, (3), pp. 657-661.*
Yokoi, H., et al. "Rapid characterization of wood extractives in wood by thermal desorption-gas chromatography in the presence of tetramethylammonium acetate." J. Anal. and Applied Pyrolysis. (2003), vol. 67, pp. 191-200.*
Zanarotti, A. "Synthesis of a Flav-3-En-3-Ol Via Cinnamylphenol." Tetrahedron Letters. (1982), vol. 23, No. 38, pp. 3963-3964.*
Bolli, A., et al. "Flavonoid binding to human serum albumin." Biochemical and Biophysical Research Communications. (2010), vol. 398, pp. 444-449.*
Marais et al., "The Stereochemisty of Flavonoids," in Erich Grotewold (ed.), *The Science of Flavonoids*, Springer, 2006, Chapter 1, pp. 1-46. (51 Total Pages).
Communication pursuant to Rules 70(2) and 70a(2) EPC, dated Aug. 12, 2014, for EP Application No. 12739384.1-1462 / 2668176, 1 page.
Extended European Search Report dated Jul. 25, 2014, for EP Application No. 12739384.1-1462 / 2668176, 6 pages.
Sweeny et al., "Synthesis of anthocyanidins—I. The oxidative generation of flavylium cations using benzoquinones," *Tetrahedron* 33(22):2923-2926, 1977.

* cited by examiner

*Primary Examiner* — Noble Jarrell
*Assistant Examiner* — John S Kenyon
(74) *Attorney, Agent, or Firm* — Seed IP Law Group PLLC

(57) ABSTRACT

The present invention provides synthetic processes for preparing racemic and/or optically pure epicatechin, epigallocatechin and related polyphenols as such or as their variously functionalized derivatives. A principle objective of the disclosure is to provide a new and useful method of synthesis to obtain polyphenols in isomerically pure and/or racemic forms.

20 Claims, No Drawings

PROCESS FOR SYNTHESIS OF POLYPHENOLS

FIELD OF THE INVENTION

The present invention provides synthetic processes for preparing racemic and/or optically pure polyphenols and their variously functionalized derivatives.

BACKGROUND OF THE INVENTION

Polyphenolic natural products are of current interest because of their numerous biological activities, their widespread occurrence in foodstuffs, and their resulting relevance for human health. Polyphenolic natural products have one or several hydroxyl groups on their aromatic rings and often an additional hydroxyl group in the 3 position. Several different hydroxylation patterns of the A and B rings have been found in nature. Representative examples include: (−)-epiafzelechin, (+)-catechin, (−)-epicatechin, (−)-gallocatechin, (−)-epigallocatechin, their respective 3-gallate esters, as well as two 3-(30-methyl)gallate esters, which are referred to collectively herein as "catechins." (+)-Catechin, (−)-catechin, (+)-epicatechin and (−)-epicatechin are flavan-3-ols, with (+)-catechin, (−)-epicatechin the most abundant. Catechins constitute about 25% of the dry weight of fresh tea leaves although the total content varies widely depending on tea variety and growth conditions. Catechins are also present in the human diet in chocolate, fruits, vegetables and wine. Catechins have found use in the treatment of acute coronary syndromes, including but not limited to myocardial infarction and angina; acute ischemic events in other organs and tissues, including but not limited to renal injury, renal ischemia and diseases of the aorta and its branches; injuries arising from medical interventions, including but not limited to coronary artery bypass grafting (CABG) procedures and aneurysm repair; cancer; and metabolic diseases, including but not limited to diabetes mellitus. Health benefits of catechins have been broadly attributed to antioxidant properties, effects on intestinal microorganisms and nutrient absorption, and effects on metabolism and metabolic enzymes.

Catechins for use as pharmaceutical and neutraceutical preparations have been obtained through plant extraction, followed if desired by purification of individual catechin species using chromatographic methods. To prove definitively the structures and to develop structure-activity relationships assigned to the compounds purified from cocoa, and other sources, comparisons must be made of defined structure prepared synthetically to polyphenols such as epicatechin. Synthetic monomers, dimers and oligomers are useful in various in vitro and ultimately in vivo models for pharmacological activity.

From a purely synthetic viewpoint, however, such molecules present difficulty in controlling the desired stereochemistry, as well as the sensitivity of the unprotected compounds to acids, bases, and oxidizing agents. There are certain processes available for the synthesis of epicatechin, however, the processes and the starting material is very costly or final product is of very low yield, leading to a very costly final product. Therefore there remains a need for efficient synthetic processes for the large scale preparation of epicatechins and catechin monomers from commercially available sources.

OBJECTIVES OF THE INVENTION

An object of the invention is to provide a novel method of synthesis to obtain polyphenols in isomerically pure and/or racemic forms.

BRIEF DESCRIPTION OF THE INVENTION

The present invention relates to a novel synthetic process for preparing polyphenols or their derivatives both as racemic mixtures and enantiomerically pure forms of Formula (I) and their pharmaceutically acceptable salts.

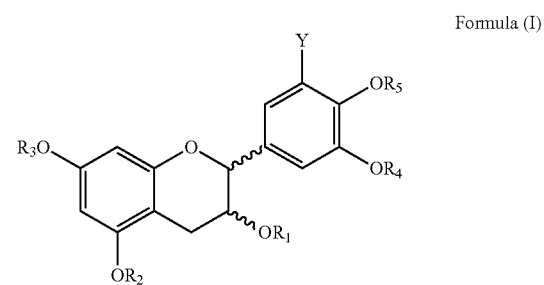

Formula (I)

Wherein
Y is selected from the group consisting of H and OR6;
R1, R2, R3, R4, R5, and R6 are independently selected from the group consisting of H, Ac, Bn, Allyl, propargyl, benzyl, 2-fluoroethyl, 4-nitrobenzyl, 4-chlorobenzyl, 4-methoxybenzyl, 4-methoxybenzonitrile, cinnamyl, methyl 4-crotonyl, but-2-en-1-yl, 2-pentenyl, (3-prop-1en-1yl)sulfonyl benzene, 1-trimethylsilyl-prop-1-yn-3-yl, 2-octyne-1-yl, 2-butyne-1-yl, 2-picolyl, 3-picolyl, 4-picolyl, quinolin-4-yl-methyl, acetonitrile, 2-methyloxirane, fluoromethyl, nitromethyl, methyl acetate-2-yl, methoxymethyl, acetamide, 1-phenylethanone-2-yl, 2-butanone-1-yl, chloromethyl, methyl phenyl sulfone, 1-bromo-prop-1-ene-3-yl, t-butyl, methyl, ethyl, allyl, trimethyl-silyl, t-butyldiphenylsilylethyl.
Formula (I) may be envisage to comprise the following compounds F1 to F4

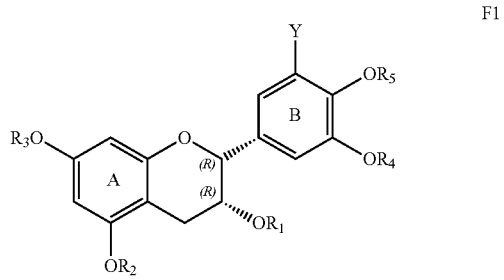

F1

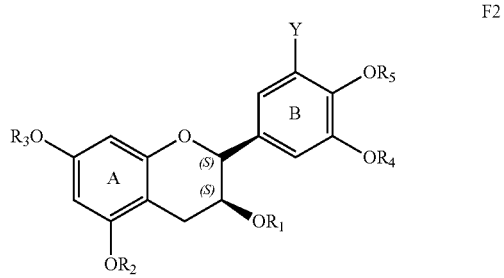

F2

-continued

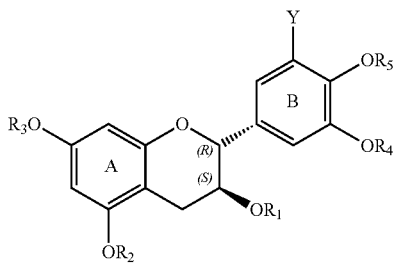
F3

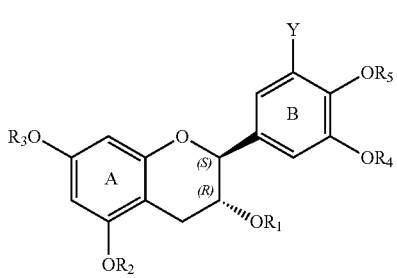
F4

Wherein Y, R1, R2, R3, R4 and R5 are as above.

DETAILED DESCRIPTION OF THE INVENTION

The present invention relates to a novel synthetic process for preparing polyphenols or their derivatives both as racemic mixtures and enantiomerically pure forms of Formula (I), their racemic mixtures, enantiomers, diastereomers and their pharmaceutically acceptable salts.

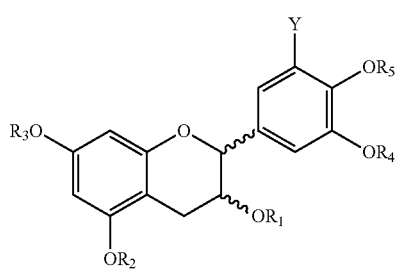
Formula (I)

Wherein

Y is selected from the group consisting of H and OR6;

R1, R2, R3, R4, R5, and R6 are independently selected from the group consisting of H, Ac, Bn, Allyl, propargyl, benzyl, 2-fluoroethyl, 4-nitrobenzyl, 4-chlorobenzyl, 4-methoxybenzyl, 4-methoxybenzonitrile, cinnamyl, methyl 4-crotonyl, but-2-en-1-yl, 2-pentenyl, (3-prop-1en-1yl)sulfonyl benzene, 1-trimethylsilyl-prop-1-yn-3-yl, 2-octyne-1-yl, 2-butyne-1-yl, 2-picolyl, 3-picolyl, 4-picolyl, quinolin-4-yl-methyl, acetonitrile, 2-methyl-oxirane, fluoromethyl, nitromethyl, methyl acetate-2-yl, methoxymethyl, acetamide, 1-phenylethanone-2-yl, 2-butanone-1-yl, chloromethyl, methyl phenyl sulfone, 1-bromo-prop-1-ene-3-yl, t-butyl, methyl, ethyl, allyl, trimethyl-silyl, t-butyldiphenylsilylethyl.

Formula (I) may be envisage to comprise the following compounds F1 to F4

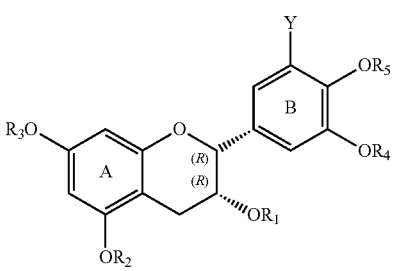
F1

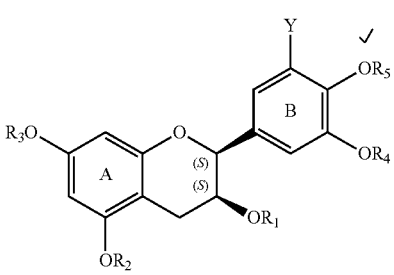
F2

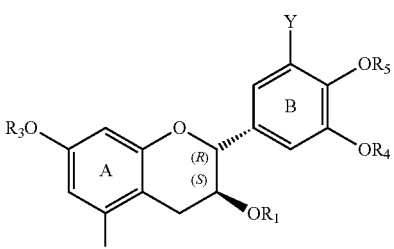
F3

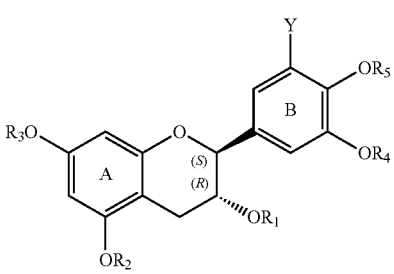
F4

Wherein Y, R1, R2, R3, R4 and R5 are as above.

The invention is directed to a novel method for preparing the compounds of Formula (I), or pharmaceutically acceptable salt(s) thereof.

The process of this invention comprises one or more of the following steps, and illustrated in Scheme 1, said process comprising the steps of:

i. protecting the hydroxyl groups of a compound of Formula (II) with one or more protecting groups, to give a compound of Formula (III);

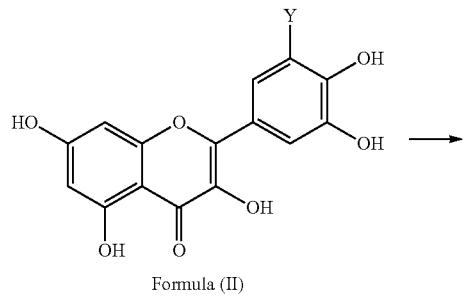

Formula (II)

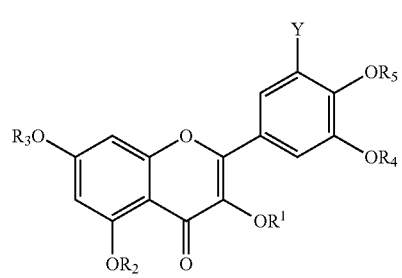

Formula (III)

ii. treating said compound of Formula (III) with a reducing agent to produce a compound selected from the group of Formula (IV), Formula (V), and Formula (VI), wherein X is selected from halide, acetate, trifloroacetate, methane sulfonate, hydroxyl etc.

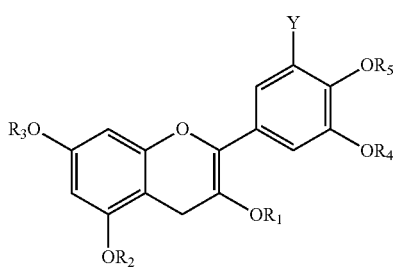

Formula (IV)

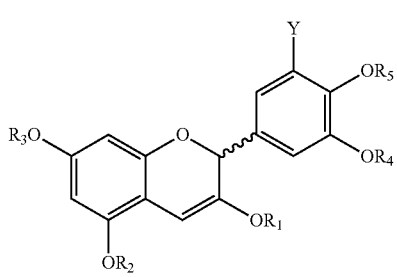

Formula (V)

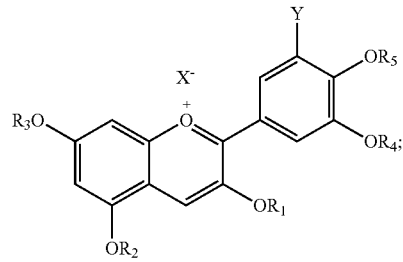

Formula (VI)

and iii. treating a compound selected from the group of Formula (IV), Formula (V), or Formula (VI) with a reducing agent to produce a compound of Formula (I).

The process of the present invention may yield pure formula (IV) or formula (V) or formula (VI) or a mixture of formula (IV) and (V).

The reduction of the compound may be chiral or achiral, that may yield a compound of Formula (I) as a single enantiomer or an enantiomerically enriched mixture, for instance the compounds R,R diastereomer (Formula (VII)), the S,S diastereomer (Formula (VIII)), or a mixture thereof:

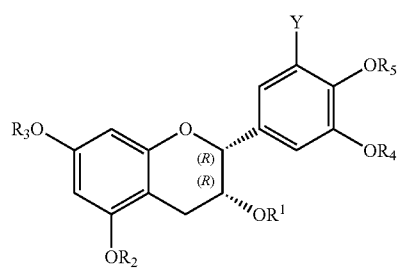

Formula (VII)

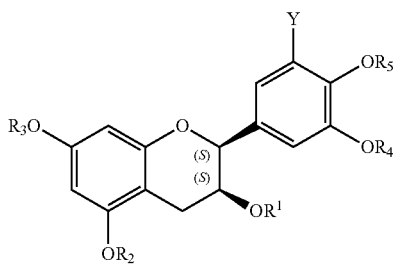

Formula (VIII)

The process of the present invention may yield compounds of Formula (I) such as (S,S)-epicatechin, (R,R)-epicatechin, a mixture of (S,S)- and (R,R)-epicatechin, (S,S)-epigallocatechin, (R,R)-epigallocatechin, and a mixture of (S,S)- and (R,R)-epigallocatechin.

The steps illustrated above are schematically represented in the general synthetic Scheme 1, and illustrate the various intermediates that are or may be involved in these conversions:

Scheme 1: General synthetic scheme illustrating the various intermediates that are or may be obtained by reduction of quercetin or related polyphenols

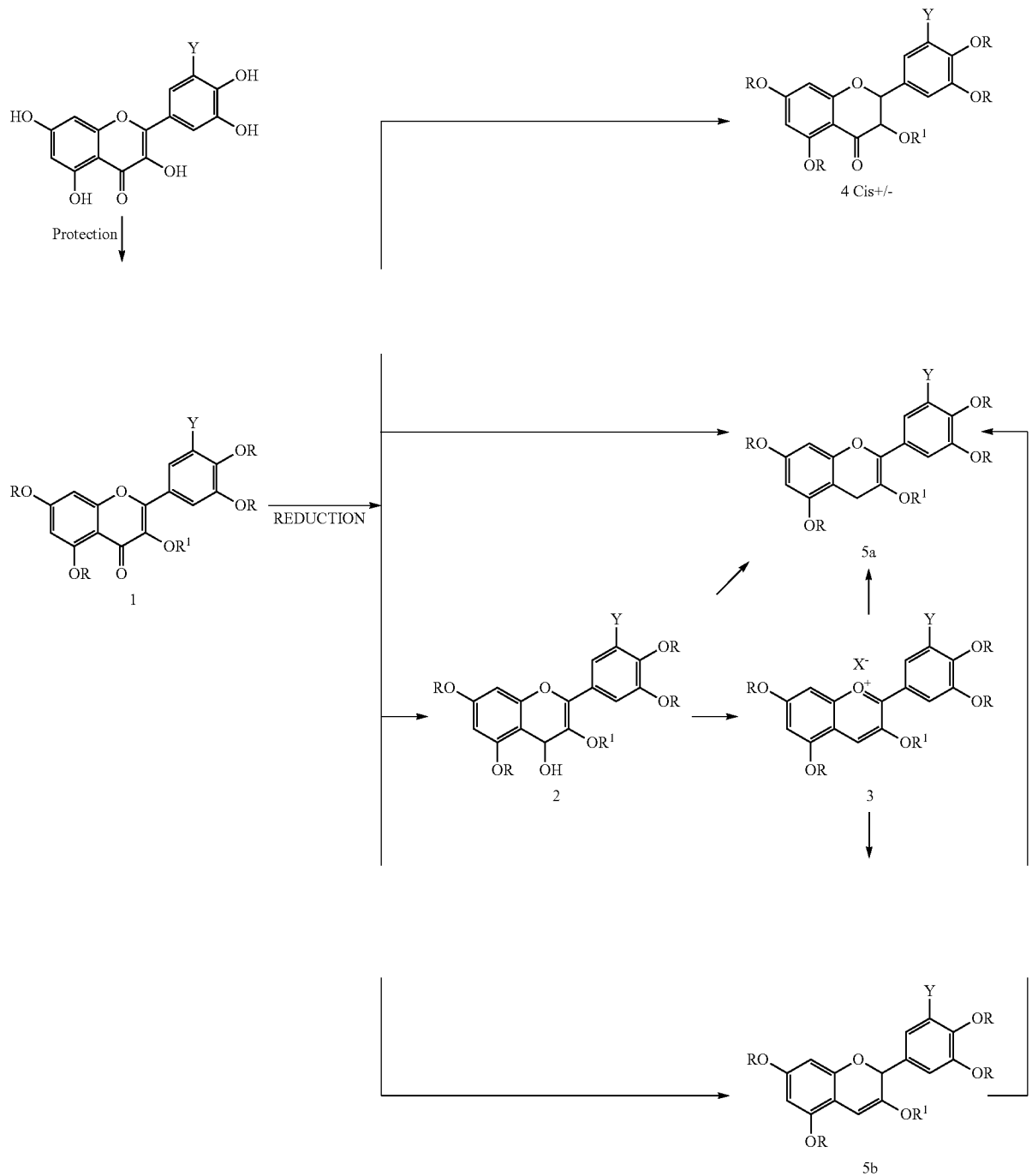

The protected starting material [1] may be reduced to compounds such as [3] directly or through the intermediate [2] using suitable reducing agents such as lithium aluminum hydride in solvent such as tetrahydrofuran and followed by treatment with an acid such as hydrochloric acid. The compound 3 may also be converted to [5a] and/or [5b] using a reducing agent such as NaCNBH₃ in a solvent such as DCM. Further allylic alcohol [2] may be converted to 5a using reagent such as triethylsilane in solvent such as tetrahydrofuran at heating. [1] may also be selectively reduced to [4] in presence of a reagent such as lithium aluminum hydride with or without copper salt as a co-catalyst in solvent such as tetrahydrofuran at a temperature ranging from 60-80° C.

The process as above may be adapted for the synthesis of epicatechin or epigallocatechin, as depicted in Scheme 2.

Scheme 2: Synthesis of Epicatechin and related polyphenols

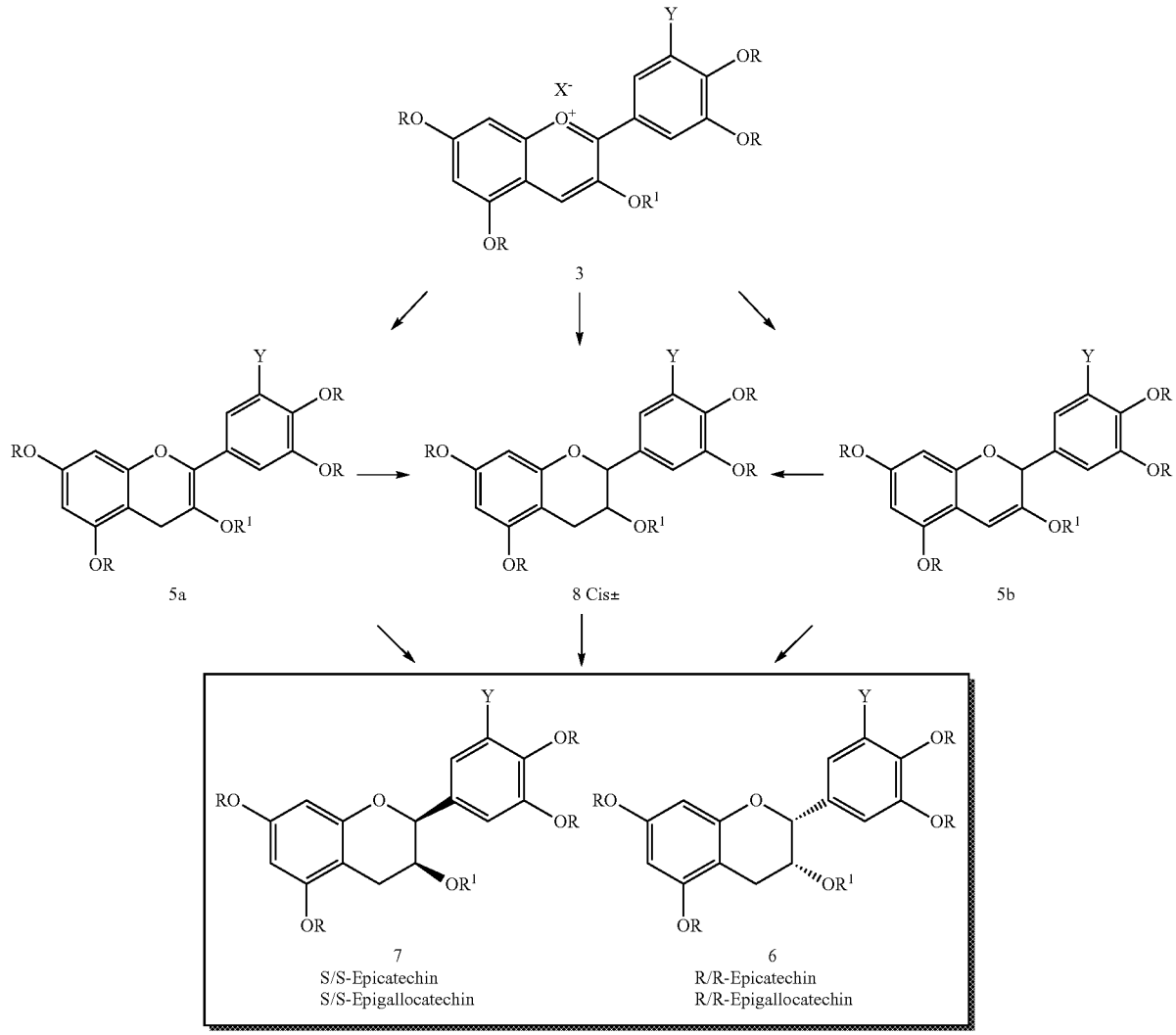

As in Scheme 2, the sequential hydrogenation and deprotection of [3] and/or [5a/b] with a reagent such as palladium on carbon in a reducing atmosphere such as hydrogen can lead to formation of racemic epicatechin or epigallocatechin [8] in major amount along with minor amount of catechin analogues. The racemic [8] can be resolved to pure enantiomer with the art known in literature such as enzymatic resolution using lipases/esterases and/or chemical resolution by making diastereoisomers with a chiral acid. Achiral hydrogenation either of [3] or [5a] and/or [5b] in the presence of catalyst such as palladium on carbon in a solvent such as ethyl acetate under reducing atmosphere such as hydrogen can provide racemic [8]. Chiral reduction either of [3] or [5a] and/or [5b] in the presence of a chiral reducing agent such as cinchona or other alkaloid-modified metal catalyst with a reducing atmosphere such as hydrogen in a solvent such as tetrahydrofuran can provide optically enriched or pure [6] or [7] as major products.

Protection of Compounds of the Present Invention

The compounds of Formula (I), that contain more than one hydroxyl group may be protected by methods suitable for protecting hydroxyl groups.

The compounds of Formula (I) may be obtained by natural sources or synthetic sources and may be either anhydrous, hydrous or as a dihydrate.

Suitable methods for protection of the hydroxyl group may be effected through alkylation, silylation, or esterification to form an ether, an ester, an acetate, a chloroacetate, a trifluoroacetate, a pivaloate, a benzoate, a 1,2-isopropylidene or a 1,3-isopropylidene.

A suitable method of protection of the hydroxyl groups involves alkylation. Alkylating agents include alkyl chlorides, bromides, iodides or alkyl sulfonates. Specific examples of alkylating agents include allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromo chloromethane, bromomethyl phenyl sulfone and 1,3-dibromo-1-propene.

A preferred reagent for alkylation may be a benzyl halide, such as benzyl bromide.

For instance, the protection of the hydroxyl group of the polyphenol by alkylation using benzyl halide as the alkylating agent is depicted at Scheme 3.

Scheme 3: Protection of hydroxyl by alkylation using benzyl halide

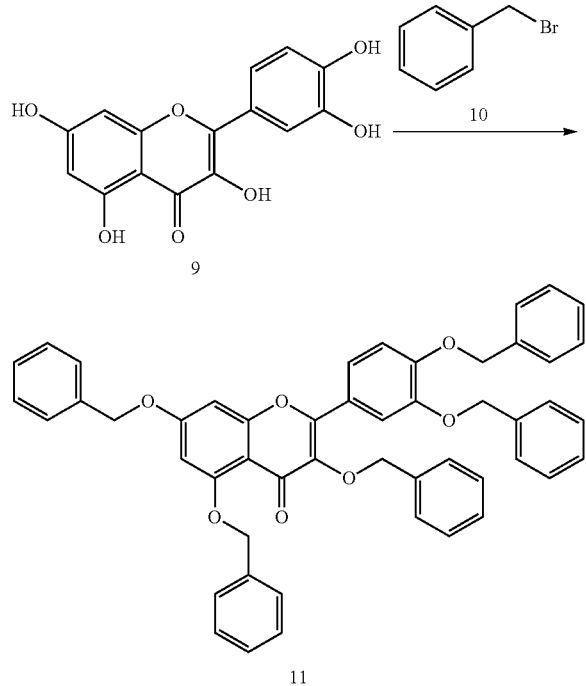

The protection of the hydroxyl group by alkylation reaction may be carried out in the presence of a strong base and a polar organic solvent.

The base may be selected from alkali metal hydride, dialkylamide, bis(trialkylsilyl)amide, carbonates or hydroxide, more preferably an alkali metal carbonate such as potassium carbonate.

The solvent may be a polar water-miscible solvent selected from acetonitrile, tetrahydrofuran (tetrahydrofuran), dimethylacetamide, dioxane, N,N-dimethylformamide, a sulfoxide such as dimethylsulfoxide, or N-methylpyrrolidinone. Preferably the solvent is dimethylformamide.

The alkylation reaction for the protection of the hydroxyl groups of quercetin [9] may be carried for a period of 4-7 hours, preferably at atmospheric pressure and at a temperature ranging from 60-80° C. by reacting with [10] to yield the protected compound [11].

Reduction of Compounds of the Present Invention

The reduction of compounds of Formula (1) may be carried out by the use of suitable reducing agents such as metal hydride which may include sodium bis(2-methoxyethoxy)aluminum hydride, lithium aluminum hydride, sodium borohydride, aluminum hydride, diisobutyl aluminum hydride, trialkoxy aluminum hydride sodium amalgam, zinc mercury amalgam and sodium bis(2-methoxyethoxy) aluminum hydride. Preferably the reducing agent is lithium aluminum hydride.

The reduction may be carried out in the presence of lewis acids such as aluminum chloride, cerium chloride, zinc chloride, boron trifluoride, iodine.

The reduction reaction may be carried out in the presence of a solvent, which may be selected from the group comprising methyl tertiary butyl ether, tetrahydrofuran, diethyl ether, toluene, acetonitrile, etc. Preferably the solvent is methyl tertiary butyl ether. The reaction may be carried out in a temperature ranging from −10° C. to 80° C.

For instance, the reduction of the compounds of Formula (I) may be illustrated by scheme 1.

Reduction and/or Deprotection of Protected Polyphenols

The reduction and deprotection may be carried out by methods such that both reactions are carried out simultaneously.

The hydrogenation catalyst is hydrogenation catalyst is selected from the group consisting of platinum, palladium, ruthenium, rhodium and nickel etc.

A preferred catalyst is by the use of hydrogen in presence of 10% palladium and carbon.

Reaction is carried out in the presence of a solvent or mixture of solvents selected from methanol, ethanol, ethyl acetate, tetrahydrofuran, acetic acid, or their mixtures, where preferably the solvent is methanol, ethanol, ethylacetate or their mixtures.

Reaction may be carried out at a temperature ranging from 25-60° C. and at a pressure ranging from 4-50 psi.

If protection of the quercetin is by benzyl groups, deprotection may be facilitated by hydrogenolylis.

It is understood that deprotection and reduction may produce catechin. Hence, it is envisaged that isomerically pure catechin and racemic catechin may be prepared by the same process as claimed in this invention and is included within the scope of this invention.

The present invention includes a process of converting the compound of Formula (VI) to the compound of Formula (IV), by the use of the reducing agent.

The reducing agent may be selected from the group comprising metal hydrides which may include sodium bis(2-methoxyethoxy)aluminum hydride, lithium aluminum hydride, sodium borohydride, sodium cyanoborohydride, aluminum hydride, isobutyl aluminum hydride, trialkoxy aluminum hydride with or without Lewis acids such as aluminum chloride, cerium chloride, zinc chloride, boron trifluoride, or iodine. Further, a suitable reducing reagent may include sodium amalgam, zinc mercury amalgam.

Preferably, the reducing agent is sodium cyanoborohydride.

The reduction reaction may be carried in the presence of a solvent selected from the group consisting of methanol, ethanol, acetic acid, ethyl acetate, methyl t-butyl ether, diethyl ether, toluene, acetonitrile or tetrahydrofuran.

The reaction may be carried out in the presence of sodium cyanoborohydride, acetic acid, and dichloromethane at a temperature of from 0° C. to 35° C.

Asymmetric Resolution of Racemic Polyphenol:

The unprotected or partially protected polyphenol may be resolved to obtain both the enantiomers in optically enriched form using asymmetric resolution technique such as:
  (i) chiral preparative liquid chromatography using an appropriate chiral phase (such as, but not limited to bonded polysaccharide chiral stationary phase)
  (ii) enzymatic hydrolysis of esters using enzymes such as, but not limited to, human or pig liver esterase
  (iii) lipase-catalyzed asymmetric trans-esterification using appropriate lipase and/or esterase.

(iv) by partial crystallization of the diastereomeric mixture of corresponding ester generated by the functionalization of one of the hydroxyl groups with optically pure acids such as mandelic or tartaric acid.

Resolution of Racemic Compounds of the Present Invention

Racemic epicatechin may be resolved by methods such as enzymatic resolution, chemical resolution, chiral column chromatography and chiral induced fractional crystallization of either unprotected or selectively protected polyphenols, as mentioned above.

In a preferred method, the racemic polyphenol may be resolved by a method comprising the steps of:

(i) protecting any four of the hydroxyl group of polyphenol by a suitable achiral protecting group, coupling the unprotected hydroxyl group with an optically pure acid to form an ester as a mixture of two diastereomers, more preferably esterification at 3 position by an optically pure-acid or activated acid to obtain an ester as a mixture of two diastereomers, (ii) separation of the two diastereoisomers of step (i) by exploiting different chemical and/or physical properties of diastereoisomers, such as fractional or preferential crystallization to obtain optically pure or diastereomerically enriched ester of preferred polyphenol, (iii) hydrolysis of the diastereomerically enriched ester to obtain enantiomerically enriched preferred polyphenol, (iv) deprotection of the enantiomerically enriched preferred polyphenol.

A suitable method of protection of the hydroxyl groups, for the resolution as disclosed above, involves alkylation. Alkylating agents include alkyl chlorides, bromides, iodides or alkyl sulfonates. Examples of alkylating agents include allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 4-bromomethyl quinoline, bromoacetonitrile, bromofluoromethane, methyl bromoacetate, methoxymethyl chloride, bromoacetamide, 2-bromoacetophenone, 1-bromo-2-butanone, bromo chloromethane, bromomethyl phenyl sulfone and 1,3-dibromo-1-propene.

A suitable reagent for alkylation may be benzyl halide, such as benzyl bromide. The protection of the hydroxyl group by alkylation reaction is carried out in the presence of a base and a polar organic solvent.

The base may be selected from the group comprising alkali metal hydride, dialkylamide, bis(trialkylsilyl)amide, carbonates or hydroxide, more preferably an alkali metal carbonate such as potassium carbonate.

The solvent may be selected from the group comprising acetonitrile, tetrahydrofuran (tetrahydrofuran), N,N-dimethylformamide, a sulfoxide such as dimethylsulfoxide, or N-methylpyrrolidinone. Preferably the solvent is dimethylformamide.

The alkylation reaction for the protection of the hydroxyl groups of epicatechin may be carried for a period of 4-7 hours preferably at atmospheric pressure and at a temperature ranging from 25-80° C.

Formation of Diastereoisomers and Separation

The protected polyphenol may be converted into its diastereoisomer by the use of chiral compounds selected from the group consisting of chiral tartaric acid or it's derivative, methoxyphenylacetic acid, 2-methoxy-2-(1-naphthyl)-propionic acid, etc. Preferably, the chiral reagent is (S and/or R)-2-methoxy-2-phenylacetic acid.

The reaction may be carried out under general reaction conditions used for esterification where a hydroxyl group of polyphenol may be esterified with a corresponding activated or un-activated acylating agent in a solvent such as tetrahydrofuran, dichloromethane, acetonitrile, dimethylformamide etc., in the presence of a base such as pyridine, triethyl amine, diisopropyl amine with or without the presence of a catalyst such 4-dimethylaminopyridine (DMAP) or N',N'-dicylcohexylcarbodiimide (DCC) at a temperature ranging from 0-50° C. Preferably the reaction conditions include the use of activated acid as acid chloride in dichloromethane as the solvent, triethyl amine as a base and 4-dimethylaminopyridine as a catalyst. The reaction may be preferably carried out at room temperature.

The diastereoisomers may be separated by any method known in the art such as column chromatography, fractional crystallization etc. Preferably, the diastereoisomers are separated by fractional crystallization.

Fractional crystallization may be achieved by solubilizing the compound in a single solvent in which the compound is freely soluble at higher temperature, but one of the diastereoisomers is insoluble at lower temperature, and thereby selectively precipitating one diastereoisomer and retaining the other in solution.

Fractional crystallization may also be achieved by solubilizing the compound in a solvent or solvents in which the compound is freely soluble and adding another solvent or solvents in which one of the diastereoisomer is insoluble and thereby selectively precipitating one diastereoisomer and retaining the other in solution.

The fractional crystallization of the polyphenol stereoisomer may be achieved by the use of any suitable solvents. Preferably, the fractional crystallization may be carried out solubilizing the compound in dichloromethane and precipitating the solution by methanol to selectively obtain one diastereomer in excess in the form of ester. This process may be repeated again to get a desire level of diastereomeric excess Hydrolysis of the Chiral Ester The chiral ester may be hydrolyzed by any method known in the art to obtain chiral purepolyphenol. A preferred method of hydrolyzing the chiral ester is by treating the diastereoisomerically pure ester with a base such as potassium carbonate in a solvent such as methanol and/or dichloromethane.

Deprotection of Optically Pure Polyphenol

In one example, optically pure benzyl protected polyphenol may be deprotected by general hydrogenolysis reaction conditions known in the art. This reaction may preferably be carried out in an atmosphere of hydrogen gas in a suitable organic solvent such as methanol, ethanol, ethyl acetate, tetrahydrofuran, acetic acid, etc. or mixtures thereof in the presence of a suitable catalyst such as palladium hydroxide, palladium on carbon at temperature range from room temperature to 60° C. Preferably the catalyst is palladium hydroxide and solvent is ethyl acetate at room temperature under a hydrogen atmosphere.

Formation of Esters and Enzymatic Separation

The protected polyphenol may be converted to an ester by esterification, using acids or acid chlorides, such as alkyl or aryl esters.

The enzymatic separation reaction may be carried out under general enzyme hydrolysis conditions known in the art used for resolving prochiral esters, for example using commercial esterases with a mixture of water-miscible or immiscible solvents such as tetrahydrofuran, acetonitrile, dimethylformamide, or ethyl acetate, etc., in the presence of base addition so as to maintain a pH range where the enzyme is still active. The reaction may be carried out at room temperature.

Once the hydrolysis has progressed to the desired point, the resulting chiral hydrolyzed protected enantiomer of polyphenol may be separated from the unreacted ester by any method known in the art such as column chromatography, fractional crystallization etc.

The process of the present invention as may be directed to a novel method for preparing epicatechin and epigallocatechin, or pharmaceutically acceptable salt(s) thereof.

The process for preparing epicatechin and epigallocatechin, comprises one or more of the following steps, and illustrated in Scheme 1:

(i) partially or fully and/or selectively protecting the hydroxyl groups of quercetin or myricetin with one or more protecting groups;
(ii) reducing the partially or fully and/or selectively protected quercetin or myricetin with a reducing agent to produce unprotected, partially or fully protected 4H chromene or 2H chromene or cyanidin or related products;
(iii) achiral reduction of unprotected, partially or fully and/or selectively protected 4H chromene or 2H chromene or cyanidin or related products and subsequent or simultaneous complete or partial deprotection of the product of this reduction to produce unprotected or partially protected racemic epicatechin or epigallocatechin;
(iv) chiral reduction of unprotected, partially or fully protected 4H chromene or 2H chromene or cyanidin or related products and subsequent or simultaneous deprotection of partially protected or fully protected product of this reduction to produce unprotected or partially protected isomerically pure epicatechin or epigallocatechin or racemic epicatechin or epigallocatechin;
(v) resolution of the product of the achiral reduction of partially or fully protected 4H chromene or 2H chromene or cyanidin or related products and subsequent or simultaneous deprotection of the product of this resolution to produce partially or fully unprotected isomerically pure epicatechin or epigallocatechin;
(vi) Resolution of the unprotected, or partially protected racemic epicatechin or epigallocatechin into isomerically pure unprotected or partially protected epicatechin or epigallocatechin.
(vii) Selective or non selective conversion of cyanidin to 4H chromene and/or 2H chromene followed by chiral or achiral reduction to epicatechin or epigallocatechin;
(viii) Conversion of 2H chromene chromene to 4H chromene followed by chiral or achiral reduction to epicatechin or epigallocatechin;

Further the steps for preparing epicatechin and epigallocatechin, are illustrated as below:

Protection of Quercetin

The protection of Quercetin may be conducted by a process as illustrated in Scheme 3.

Reduction of Protected Quercetin to 4H Chromene

Scheme 4:

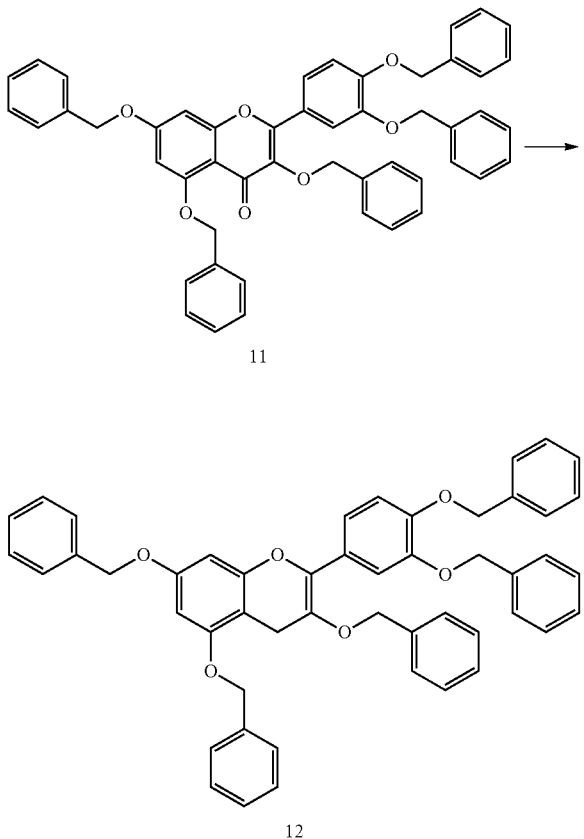

The protected quercetin [11] (pentabenzyl quercetin; 3,5,7-tris(benzyloxy)-2-(3,4-bis(benzyloxy)phenyl)-4H-chromen-4-one) is reduced by suitable reducing agents as described above to obtain protected 4H chromene [12] 3,5,7-tris(benzyloxy)-2-(3,4-bis(benzyloxy)phenyl)-4H-chromene.

Synthesis of Epicatechin by Reduction and Deprotection of Protected 4H Chromene

The synthesis of racemic epicatechin [13] by reduction and deprotection of 4H chromene is illustrated in Scheme 5. The protected 4H chromene [12] may be simultaneously reduced and deprotected or sequentially reduced and deprotected as shown in the general synthetic Scheme 5. Further the reduction of chromene may be carried out in the presence of a chiral catalyst and/or chiral auxiliary known in the art, to provide isomerically enriched reduced product. The preferred method is the simultaneous reduction and deprotection of cyanidin.

This reaction may preferably be carried out in an atmosphere of hydrogen gas in a suitable organic solvent such as methanol, ethanol, ethyl acetate, tetrahydrofuran, acetic acid etc. or mixtures thereof in the presence of a suitable catalyst such as Pd, Pt, Ni etc. adsorbed onto a solid support.

Scheme 5: Synthesis of racemic epicatechin by reduction and deprotection of 4H chromene

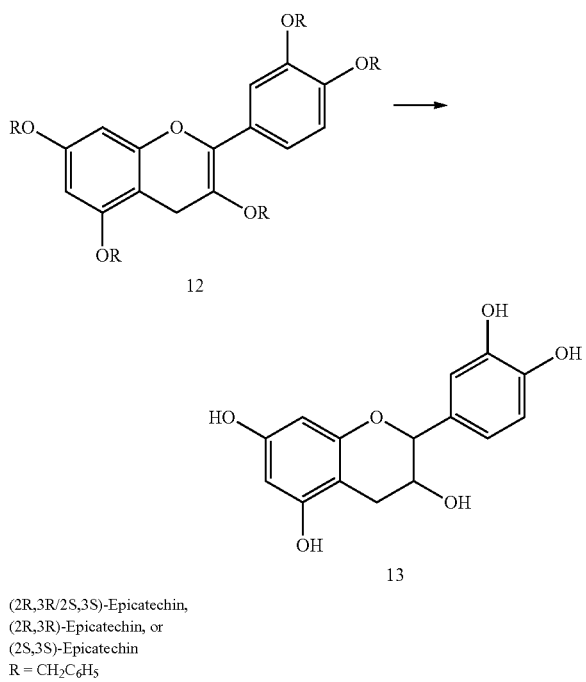

12

13

(2R,3R/2S,3S)-Epicatechin,
(2R,3R)-Epicatechin, or
(2S,3S)-Epicatechin
R = CH$_2$C$_6$H$_5$ The Reduction and Protection of 4H Chromene May be Carried Out by Methods as Above.

Reduction of Protected Quercetin to Cyanidin

Scheme 6:

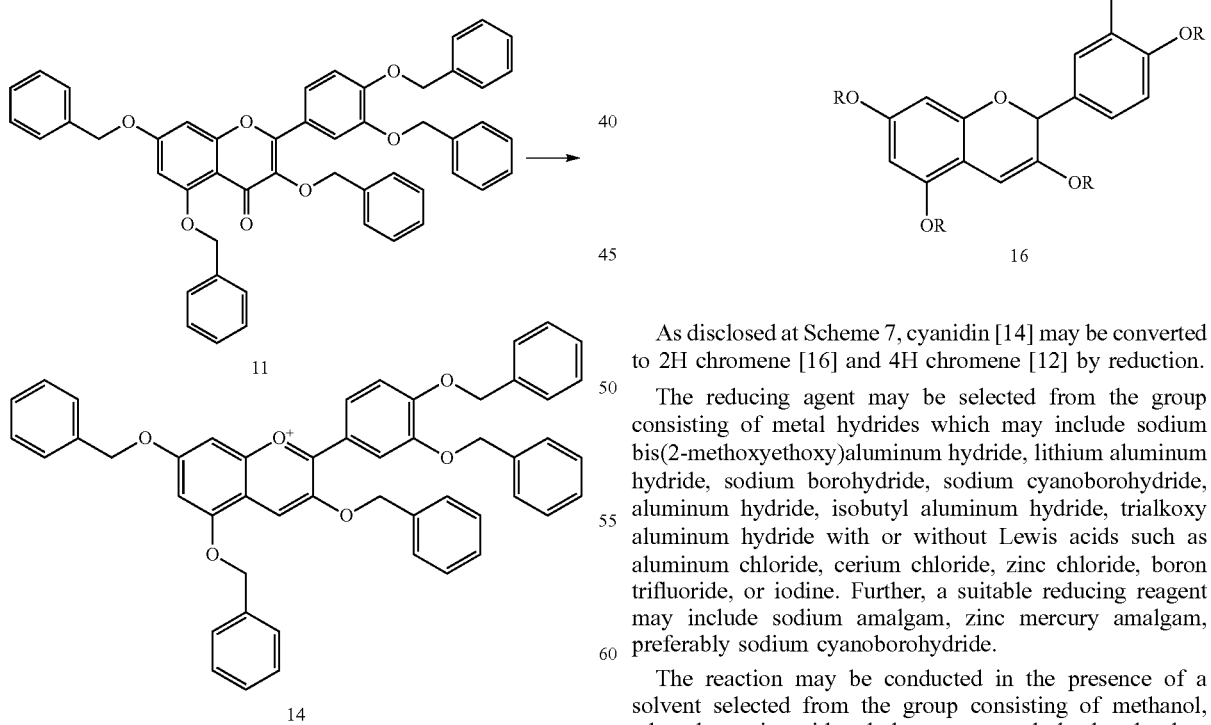

11

14

The protected quercetin [11] (pentabenzyl quercetin; 3,5, 7-tris(benzyloxy)-2-(3,4-bis(benzyloxy)phenyl)-4H-chromen-4-one) is reduced by suitable reducing agents to obtain protected cyanidin [14] (3,5,7-tris(benzyloxy)-2-(3, 4-bis(benzyloxy)phenyl)chromenylium).

Conversion of Cyanidin to 4H and/or 2H Chromene:

The conversion of cyanidin is illustrated in scheme 7. The protected cyanidin can be converted to of 4H chromene and 2H chromene using a suitable reducing agent. Further, reaction conditions can be optimized to get either 4H chromene or 2H chromene as an exclusive product.

Scheme 7

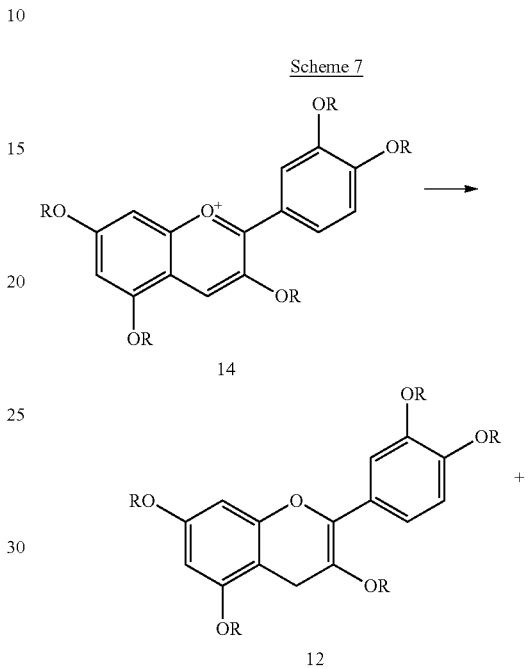

14

12

16

As disclosed at Scheme 7, cyanidin [14] may be converted to 2H chromene [16] and 4H chromene [12] by reduction.

The reducing agent may be selected from the group consisting of metal hydrides which may include sodium bis(2-methoxyethoxy)aluminum hydride, lithium aluminum hydride, sodium borohydride, sodium cyanoborohydride, aluminum hydride, isobutyl aluminum hydride, trialkoxy aluminum hydride with or without Lewis acids such as aluminum chloride, cerium chloride, zinc chloride, boron trifluoride, or iodine. Further, a suitable reducing reagent may include sodium amalgam, zinc mercury amalgam, preferably sodium cyanoborohydride.

The reaction may be conducted in the presence of a solvent selected from the group consisting of methanol, ethanol, acetic acid, ethyl acetate, methyl t-butyl ether, diethyl ether, toluene, acetonitrile or tetrahydrofuran or their mixture. Preferably the solvent is a mixture of acetic acid and dichloromethane at a temperature of from 0° C. to 35° C.

Conversion of 2H Chromene to 4H Chromene

In another aspect the 4H chromene to 2H chromene may be converted to 2H chromene as below at Scheme 8.

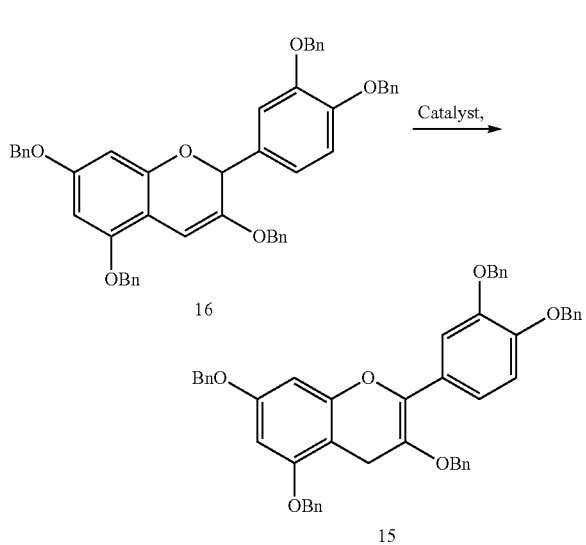

2H chromene may be converted to 4H chromene by the use of a catalyst.

Catalyst may be a lewis acid such as aluminum chloride, cerium chloride, zinc chloride, boron trifluoride and/or iodine or a mild acid such as para-toluenesulfonic acid in a solvent such as THF, toluene, xylene, nitrobenzene etc at a temperature ranging from 20 to 150° C.

Synthesis of Epicatechin by Reduction and Deprotection of Protected Cyanidin

The synthesis of racemic epicatechin [13] by reduction and deprotection of cyanidin is illustrated in Scheme 9. The protected cyanidin [14] may be simultaneously reduced and deprotected or sequentially reduced and de-protected as shown in the general synthetic Scheme 9. Further the reduction of cyanidin could be carried out in the presence of a chiral catalyst and/or chiral auxiliary known in the art, to provide isomerically enriched reduced product. The preferred method is the simultaneous reduction and deprotection of cyanidin. This reaction may preferably be carried out in an atmosphere of hydrogen gas in a suitable organic solvent such as methanol, ethanol, ethyl acetate, tetrahydrofuran, acetic acid etc. or mixtures thereof in the presence of a suitable catalyst such as Pd, Pt, Ni etc. adsorbed onto a solid support.

Scheme 9: Synthesis of racemic epicatechin by reduction and deprotection of cyanidin

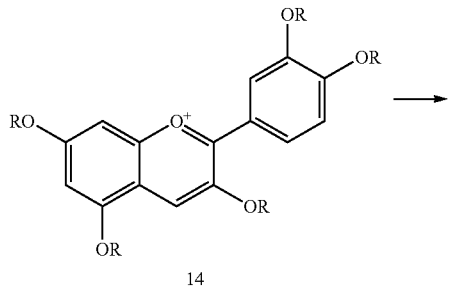

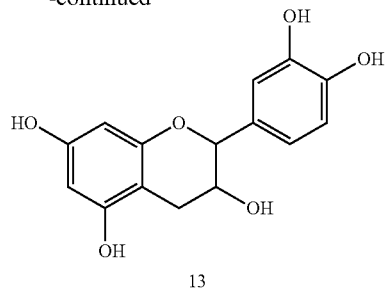

(2R,3R/2S,3S)-Epicatechin,
(2R,3R)-Epicatechin, or
(2S,3S)-Epicatechin
R = CH$_2$C$_6$H$_5$ Asymmetric Resolution of Racemic Epicatechin and/or Epigallocatechin and Related Polyphenols:

The unprotected or partially protected racemic epicatechin and/or epigallocatechin or related phenols can be resolved to get both the enantiomers in optically enriched form using asymmetric resolution technique known in the art such as:

(i) chiral preparative liquid chromatography using an appropriate chiral phase (such as, but not limited to bonded polysaccharide chiral stationary phase)

(ii) enzymatic hydrolysis of esters using enzymes such as, but not limited to, human or pig liver esterase (iii) lipase-catalyzed asymmetric trans-esterification using appropriate lipase and/or esterase.

(iv) by partial crystallization of the diastereomeric mixture of corresponding ester generated by the functionalization of one of the hydroxyl groups with optically pure acids such as mandelic or tartaric acid.

In cases the product is the ester of the desired isomer, the final product, in this instance epicatechin or epigallocatechin can be obtained by the hydrolysis of the ester moiety by acid catalyzed hydrolysis or base catalyzed hydrolysis by methods Resolution of Compounds of the Present Invention The compounds of the present invention may be reloved by the method comprising the steps of:

(i) protecting all but one of the hydroxyl groups of the compound of Formula (I) using one or more achiral protecting groups;

(ii) coupling the unprotected hydroxyl group with an optically pure acid to form an ester as a mixture of two diastereomers;

(iii) separation of the two diastereoisomers formed in step (ii) by fractional or preferential crystallization to obtain an optically pure or diastereomerically enriched ester;

(iv) hydrolysis of the optically pure or diastereomerically enriched ester to obtain an enantiomerically enriched protected compound; and (v) deprotection of the enantiomerically enriched protected compound to give a compound of Formula (I).

The resolution may be carried out such that the esterification occurs at step (v)

The racemic epicatechin may be resolved by any method known in the art such as enzymatic resolution, chemical resolution, chiral column chromatography and chiral induced fractional crystallization of either unprotected or selectively protected epicatechin, as mentioned above.

In a preferred method, the compound of formula (II) is a racemic quercetin or myricetin.

The resolution of racemic myricetin or quercetin may be carried out by:
  i. protecting any four of the hydroxyl groups of epicatechin;
  ii. coupling the unprotected hydroxyl group with an optically pure acid to form an ester as a mixture of two diastereomers;
  iii. separation of the two diastereoisomers to provide a diastereomerically enriched ester;
  iv. hydrolysis of the diastereomerically enriched ester to obtain enantiomerically enriched protected epicatechin; and
  v. deprotection of the enantiomerically enriched protected epicatechin to provide epicatechin as a substantially pure enantiomer or an enantiomerically enriched mixture.

The protection at step (i) of the resolution of quercetin and myricetin may be 5,7,3',4'hydroxyl groups of epicatechin.

The esterification may be carried out preferably at 3 position by an optically pure-acid or activated acid to obtain an ester as a mixture of two diastereomers.

Formation of Diastereoisomers and Separation

The protected epicatechin may be converted to its diastereoisomer by the use of chiral compounds selected from the group consisting of chiral tartaric acid or it's derivative, methoxyphenylacetic acid, 2-methoxy-2-(1-naphthyl)-propionic acid, etc. Preferably, the chiral reagent is (S and/or R)-2-methoxy-2-phenylacetic acid.

The diastereoisomers may be separated by any method known in the art such as column chromatography, fractional crystallization etc. Preferably, the diastereoisomers are separated by fractional crystallization.

Hydrolysis of the Chiral Ester

The chiral ester may be hydrolyzed by any method known in the art to obtain chiral pure epicatechin. A preferred method of hydrolyzing the chiral ester may be by treating the diastereoisomerically pure ester with a base such as potassium carbonate in a solvent such as methanol and/or dichloromethane.

Deprotection of Optically Pure Epicatechin

In one example, optically pure benzyl protected epicatechin may be deprotected by general hydrogenolysis reaction conditions known in the art.

Formation of Esters and Enzymatic Separation

The protected epicatechin may be converted to an ester by esterification, using acids or acid chlorides, such as alkyl or aryl esters.

In another aspect, the present invention is drawn to the intermediates of the novel process of synthesis of polyphenols. In particular, this aspect discloses the unprotected, partially protected and completely protected 4H chromene [formula (II)] and 2H chromene[formula (III)] structures of as below:

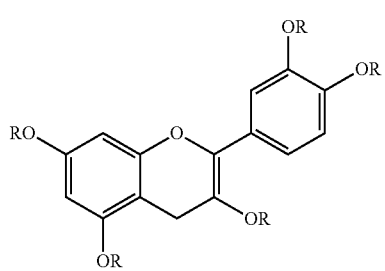

Formula (II)

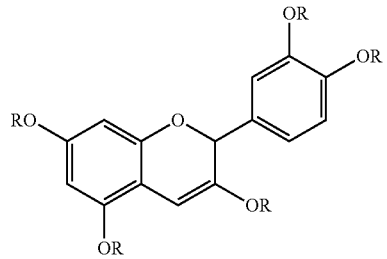

Formula (III)

Wherein R is selected from H, $CH_3$, Bn, Ac, $Si(CH_3)_3$, allyl.

In yet another aspect, the present invention is drawn to the use of 4H chromene and 2H chromene in the synthesis of epicatechin.

In another aspect, the invention is directed to methods of preparing pharmaceutical or nutraceutical compositions comprising catechin and/or epicatechin. These methods comprise preparing catechin and/or epicatechin, or pharmaceutically acceptable salt(s) thereof, by the methods described herein and combining this with a pharmaceutically or neutraceutially acceptable carrier.

In a related aspect, the invention is directed to methods of administering such a pharmaceutical or nutraceutical composition to a subject in need thereof. Routes of administration for the pharmaceutical and nutraceutical compositions of the present invention include parenteral and enteral routes. Preferred enteral routes of administration include delivery by mouth (oral), nasal, rectal, and vaginal routes. Preferred parenteral routes of administration include intravenous, intramuscular, subcutaneous, and intraperitoneal routes.

Preferably, the pharmaceutical or nutraceutical compositions of the present invention are administered in an "effective amount." This term is defined hereinafter. Unless dictated otherwise, explicitly or otherwise, an "effective amount" is not limited to a minimal amount sufficient to ameliorate a condition, or to an amount that results in an optimal or a maximal amelioration of the condition. In the case when two or more pharmaceuticals are administered together, an effective amount of one such pharmaceutical may not be, in and of itself be an effective amount, but may be an effective amount when used together with additional pharmaceuticals.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

EXPERIMENTAL

Example 1

Synthesis of Pentabenzylated Quercetin

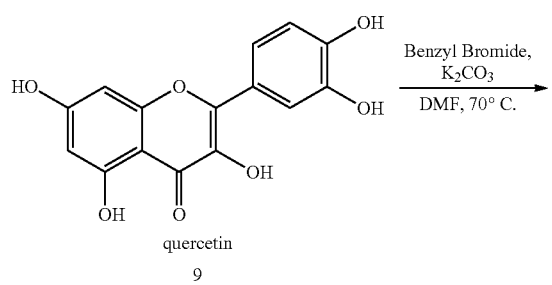

quercetin
9

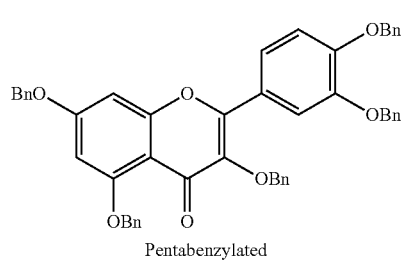

Pentabenzylated
11

To a solution of quercetin [9] (5 g) in dimethylformamide (30 ml) was added potassium carbonate (34.3 gm) followed by drop wise addition of benzyl bromide (23.7 ml) at room temperature. The reaction mixture was heated at 70° C. for 15 hours and then cooled to room temperature, to which was added water (60 ml) and the stirring was continued for an additional hour. The precipitated solid was filtered, washed five times with water and twice with ethyl acetate to give 10 g (80%) of desired product [11].

Analytical Data:
ESIMS: 753 (M$^+$+1)

Example 2

Synthesis of Pentabenzylated Cyanidin

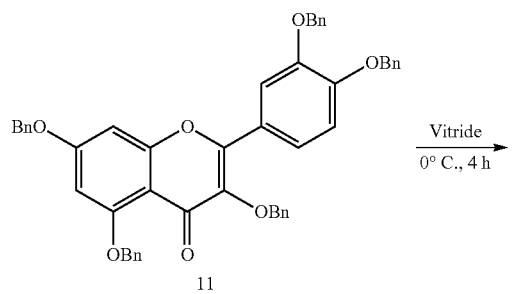

11

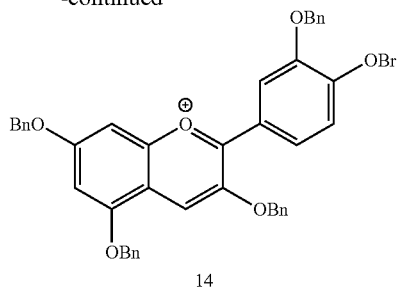

14

To a stirred solution of [11] (25 g, 0.0332 mol) in dry tetrahydrofuran under nitrogen atmosphere was added Vitride solution (56 ml, 0.166 mmol) at 0-5° C. over a period of 5 min. The reaction was stirred at this temperature for 4 h. After completion of reaction the reaction mixture was quenched with saturated NaCl solution under cooling. Reaction mixture was further diluted with ethylacetate, organic layer was separated, dried over sodium sulfate and evaporated under reduced pressure to give crude pale yellow gummy mass (30.0 g). The above crude mass was purified by column chromatography on silica using ethylacetate/hexane as eluent to afford yellow gummy mass (15.0 gm) which was further treated with methanolic HCl at 0-5° C. for 2 h and then at 25-30° C. for 24 h. The wet cake obtained was dried under vacuum to afford [14] as pinkish solid.

Analytical Data:
ESIMS: 738 [M$^+$+1]

Example 3

Synthesis of (±)-Epicatechin from cyanidin

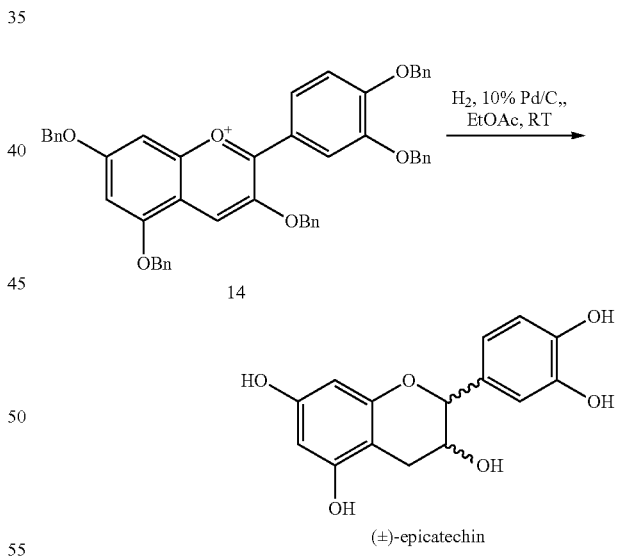

The crude pentabenzylated cyanidin [14] (2 g) was taken in ethyl acetate (30 ml) and a slurry of 10% Pd/C dry (0.2 g) in methanol (10 ml) was added to it under nitrogen atmosphere. The resultant solution was stirred under hydrogen pressure using balloon for 5 hours at 50° C. Filtration through Celite under suction and concentration of the filtrate gave a crude solid material (0.7 g). The solid material was taken in acetone (30 ml) and filtered through filter paper. The filtrate was concentrated to yield 0.2 g crude (+/−) epicatechin [13].

Analytical data:
 ESIMS: 291 (M⁺+1)

Example 4

Synthesis of 4H-chromene [15] and/or 2H-chromene [16] from quercetin

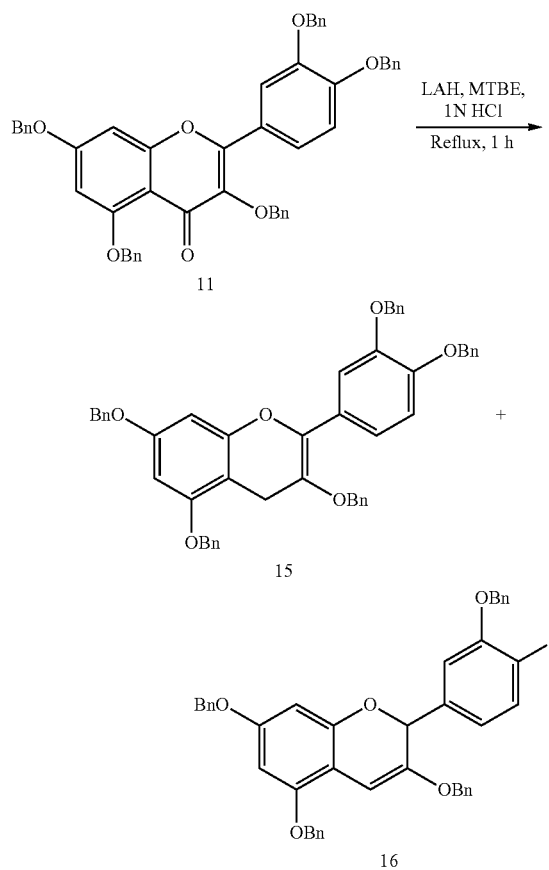

To a stirred suspension of [11] (2.5 g) in methyl tertiary butyl ether (75.0 ml) was added lithium aluminum deuteride (0.251 mg, 3.6 eq)) in portion at room temperature under nitrogen atmosphere. After stirring for 10 min at this temperature, temperature of reaction was raised to 65-70° C. After stirring at same temperature for 1 h, reaction mass was quenched with 1N HCl (10 ml) solution at 0-5° C. then the temperature of reaction mass was raised to room temperature. Ethyl acetate (10 ml) was added to the reaction mass and stirred for 30 min, then organic layer was decanted, aqueous layer was diluted with ethyl acetate, filtered through celite bed, separated both aqueous and organic layers. Combined organic layers were concentrated under reduced pressure to afford off white solid (2.5 g). Above crude compound was triturated with ethyl acetate (10 ml) at room temperature for 4 h and then filtered, washed with ethyl acetate, dried under vacuum to afford 1.0 g (40%) of off-white solid [4]. After isolation of [4], mother liquor was concentrated under reduced pressure to afford pale yellow color residue. The semi solid obtained was triturated with 50% ethyl acetate: hexane (250 ml) for 30 min at room temperature yielding a solid. The solid was further filtered and washed with 50% ethyl acetate:hexane (200 ml). The solid was dried under vacuum to obtain the product as an off-white solid (0.250 g, 10%) [16].

Analytical Data:
 ESIMS: 739 [M⁺+1]

Example 5

Synthesis of racemic epicatechin [13] from 4H-chromene [15]

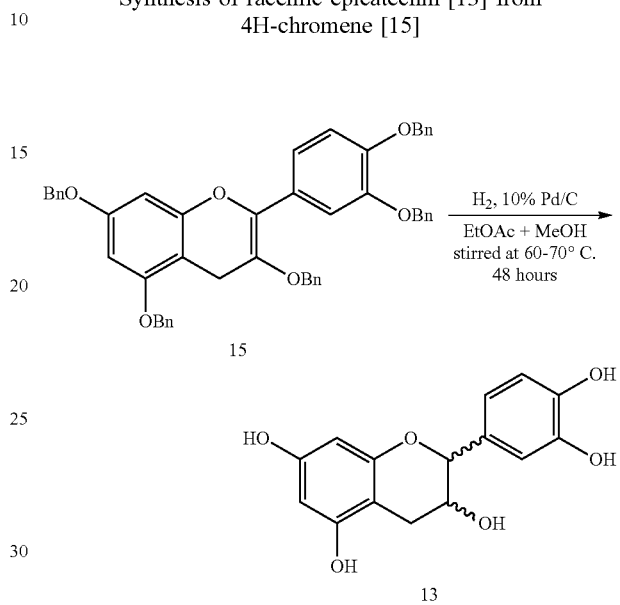

General Procedure:

To a stirred solution of [15] (5.00 g, 6.7 mmol) in a 1:1 mixture of methanol and ethyl acetate (30 ml) was added a slurry of 10% Pd/C dry (0.5 g) in methanol (5 ml) under nitrogen atmosphere. The resultant solution was stirred under hydrogen pressure at 60-70° C. for 48 h.

After completion of reaction, reaction mixture was filtered through Celite bed under suction and concentration of the filtrate gave a crude solid material (2.2 g, 110%). The solid material was purified by column chromatography using methanol/dichlormethane as eluent to obtained pure [13] (1.65 g, 66%). The solid obtained was further re-crystallized from water (10 ml) to afford a light pink solid.

Analytical Data:
 ESIMS: 291 [M⁺+1]

Example 6

Synthesis of racemic epicatechin and racemic catechin from 2H-chromene [16]

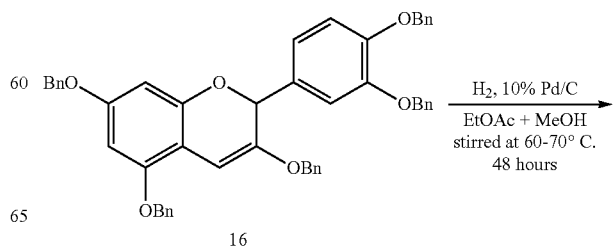

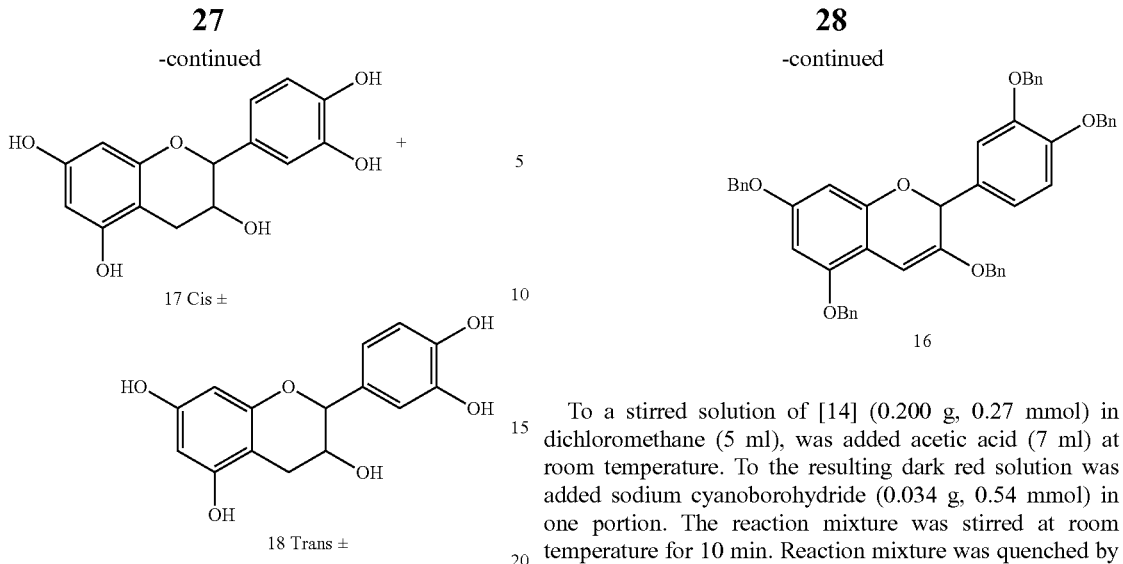

17 Cis ±

18 Trans ±

General Procedure:

To a stirred solution of [16] (5.00 g, 6.77 mmol) in a 1:1 mixture of methanol and ethyl acetate (30 ml) was added a slurry of 10% Pd/C dry (0.5 g) in methanol (5 ml) under nitrogen atmosphere. The resultant solution was stirred under hydrogen pressure at 60-70° C. for 48 h. After completion of the reaction, the reaction mixture was filtered through a Celite bed under suction and concentration of the filtrate under diminished pressure afforded crude solid material (2.23 gm). The solid material was purified by column chromatography using methanol/dichloromethane as eluent to obtain [2] and [4] (1.4 gm, 66%). The above obtained solid was separated by prep HPLC.

Product: 1) Racemic Epicatechin [17]: 0.960 g (49%).
2) Racemic Catechin [18]: 0.150 g (8%).
Analytical Data:
ESIMS: 291 [M$^+$+1]

Example 7

Synthesis of 4H-chromene [16] and/or 2H-chromene [14] from cyanidin

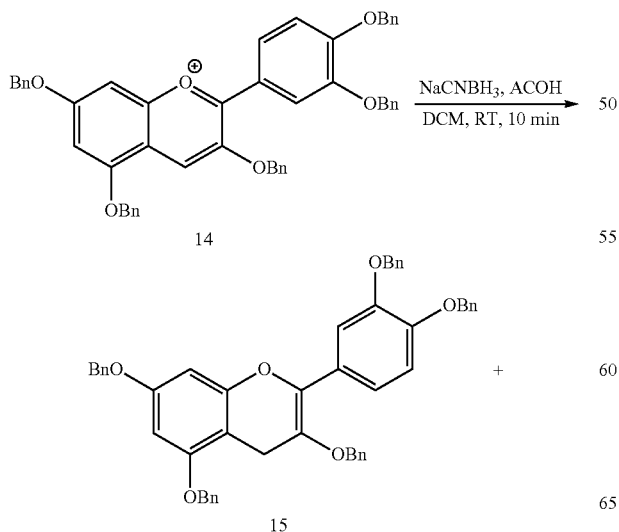

To a stirred solution of [14] (0.200 g, 0.27 mmol) in dichloromethane (5 ml), was added acetic acid (7 ml) at room temperature. To the resulting dark red solution was added sodium cyanoborohydride (0.034 g, 0.54 mmol) in one portion. The reaction mixture was stirred at room temperature for 10 min. Reaction mixture was quenched by addition of water (10 ml) and extracted by ethyl acetate (50 ml×2). The organic layer was evaporated under diminished pressure to afford light yellow solid. The solid was re-crystallized from ether and pentane to afford an off-white solid [15 and 16] (0.150 g, 75%).
Analytical Data:
ESIMS: 739 [M$^+$+1]

Example 8

Synthesis of (±)-5,7,3',4'-Tetra-O-benzyl-epicatechin [19]

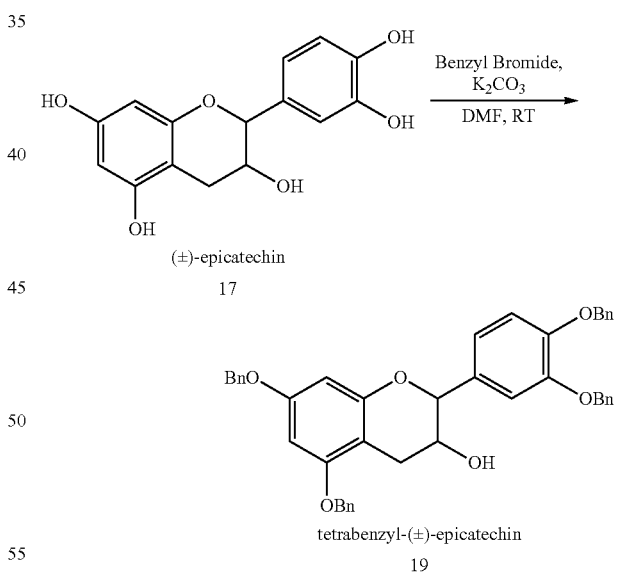

To the solution of (±)-epicatechin [17] (0.500 g, 1.724 mmol) in dimethylformamide (5.0 ml) was added potassium carbonate (1.43 g, 10.345 mmol) followed by drop wise addition of benzyl bromide (0.88 ml, 7.241 mmol) at room temperature. The reaction mixture was stirred at RT for 20 h and quenched with water (6 ml). Product was extracted using ethyl acetate. The organic layer was washed with water and dried over anhydrous sodium sulfate. Removal of excess solvent under vacuum on Rotavapor provided 1.1 g (98% yield) of desired product. The crude solid was purified by column chromatography using 5 to 15% ethyl acetate in cyclohexane to yield the desired product [19] as a solid (0.7 g, 78%, >85% purity).
Analytical data:
ESIMS: 651 (M⁺+1)
¹H-NMR (CDCl₃, 300 MHz): δ (ppm) 7.47-7.311 (m, 20H), 7.14-7.15 (d, 1H, J=1.5 Hz), 7.00-6.99 (d, 1H, J=1.5 Hz), 6.98 (s, 1H), 6.28 (s, 1H), 6.27 (s, 1H), 5.21 (s, 2H), 5.19 (s, 2H), 5.02 (s, 2H), 5.01 (s, 2H), 4.94-4.92 (d, 1H, J=6.0), 4.22 (m, 1H), 4.06 (s, 1H), 3.08-2.98 (dd, 1H, J=2.4, 17.1) 2.96-2.89 (dd, 1H, J=4.5, 17.7).

Example 9

Synthesis of (S)-(2R,3R)-5,7-bis(benzyloxy)-2-(3', 4'-bis(benzyloxy)phenyl)chroman-3-yl2-methoxy-2-phenylacetate [21]

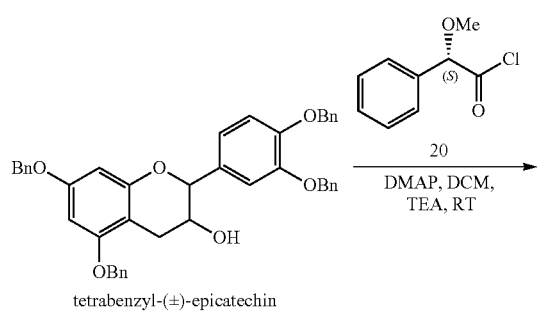

tetrabenzyl-(±)-epicatechin
19

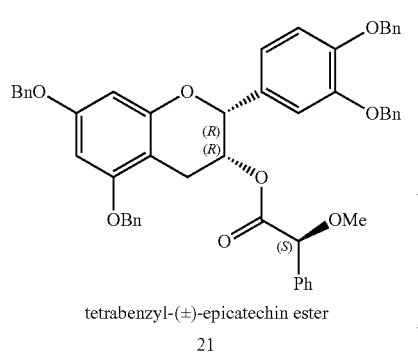

tetrabenzyl-(±)-epicatechin ester
21

To a stirred solution of (±)-5,7,3',4'-tetra-O-benzyl-epicatechin [19] (0.500 g, 0.768 mmol), triethylamine (0.64 ml, 4.61 mmol) and dimethylaminopyridine (0.025 g in 5 ml dry dichloromethane), was added drop wise a freshly prepared solution of (S)-2-methoxy-2-phenylacetyl chloride [20] (0.426 g, 2.31 mmol) in dichloromethane slowly at room temperature under nitrogen. [(S)-2-methoxy-2-phenylacetyl chloride [20] was separately prepared by stirring (S)-2-methoxy-2-phenylacetic acid and thionylchloride in dry dichloromethane with catalytic amount of dimethylformamide for 30 min. and removing the excess thionylchloride and dichloromethane by under vacuum]. After the addition, the reaction mixture was stirred at 40° C. for 5 to 6 hours and monitored by TLC. On complete consumption of the starting material, the reaction mixture was cooled to ambient temperature and the organic layer was washed with water followed by brine solution. The organic layer was dried over anhydrous sodium sulfate and concentrated under vacuum to yield 0.500 g of a thick viscous semi solid. This viscous solid was treated with methanol (5 ml) to yield solid precipitate. The precipitate was filtered to give [21] as a solid (0.235 g) which was enriched in the desired diastereoisomer with a diastereomeric excess of ~85% based on HPLC and ¹H NMR analysis.

Fractional Crystallization of Diastereomers 50 mg of this enriched solid was dissolved in a minimum amount of dichloromethane to make a clear solution. Addition of methanol was done dropwise to make it turbid and left overnight at ambient temperature (27° C.) to yield precipitates which were filtered off and dried to give 25 mg of product with diastereomeric excess of >95% as determined by analytical HPLC and ¹H NMR analysis. The absolute conformation of major diastereoisomer was determined by HPLC comparison with authentic sample of (S)-(2R,3R)-5,7-bis(benzyloxy)-2-(3',4'-bis(benzyloxy)phenyl)chroman-3-yl-2-methoxy-2-phenylacetate made from commercially available (2R,3R)-epicatechin.
Analytical Data:—
ESIMS: 799.8 (M⁺+1)
¹H-NMR (CDCl₃, 300 MHz): δ (ppm) 7.48-6.92 (m, 28H), 6.27-6.26 (d, 1H, J=2.1 Hz), 6.20-6.19 (d, 1H, J=2.1 Hz), 5.45 (m, 1H), 5.17 (s, 4H), 5.01-5.04 (d, s, 3H), 4.93-4.82 (dd, 2H, J=11.7, 21.6), 4.57 (s, 1H) 3.17 (s, 3H), 2.87-2.79 (dd, 1H, J=4.2, 16.2) 2.72-2.65 (dd, 1H, J=3.3, 15.6).

Example 10

Synthesis of (2R,3R)-5,7,3',4'-Tetra-O-benzyl-epicatechin [23]

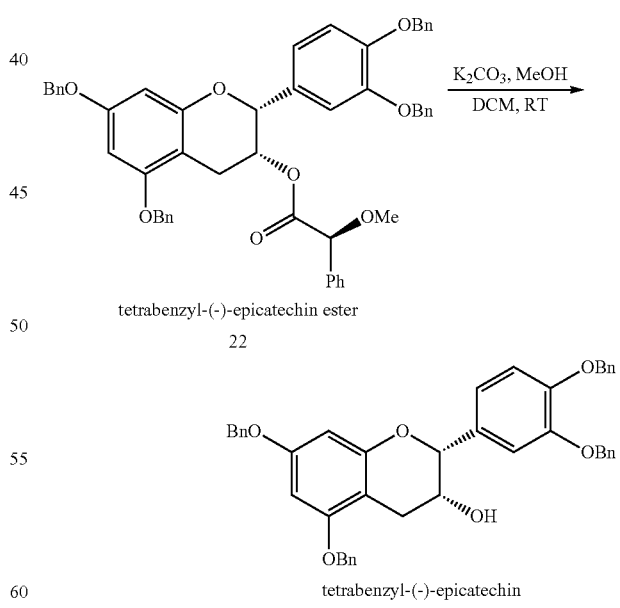

To a stirring solution of (S)-(2R,3R)-5,7-bis(benzyloxy)-2-(3',4'-bis(benzyloxy)phenyl)chroman-3-yl 2-methoxy-2-phenylacetate [22] (0.100 g, 0.125 mmol) in methanol (1 ml) and dichloromethane (2 ml) was added potassium carbonate (0.052 g, 0.376 mmol) at ambient temperature and the resulting mixture was stirred for 25 to 30 hours at ambient temperature. After completion of reaction by TLC analysis, excess of solvent was distilled off and the crude solid was dissolved in dichloromethane and washed with water followed by saturated brine solution. The organic layer was separated and the solvent was removed under vacuum after drying over sodium sulphate to yield crude of (2R,3R)-5,7,3',4'-tetra-O-benzyl-epicatechin [23] (0.070 g).

Analytical Data:

ESIMS: 651 (M$^+$+1)

$^1$H-NMR (CDCl$_3$, 300 MHz): δ (ppm) 7.47-7.311 (m, 20H), 7.14-7.15 (d, 1H, J=1.5 Hz), 7.00-6.99 (d, 1H, J=1.5 Hz), 6.98 (s, 1H), 6.28 (s, 1H), 6.27 (s, 1H), 5.21 (s, 2H), 5.19 (s, 2H), 5.02 (s, 2H), 5.01 (s, 2H), 4.94-4.92 (d, 1H, J=6.0), 4.22 (m, 1H), 4.06 (s, 1H), 3.08-2.98 (dd, 1H, J=2.4, 17.1), 2.96-2.89 (dd, 1H, J=4.5, 17.7).

Example 11

Synthesis of (−)-Epicatechin [24]

To a stirred solution of (2R,3R)-5,7,3',4'-tetra-O-benzyl-epicatechin [23] (0.07 g, 0.108 mmol) in ethyl acetate (5 ml), was added a slurry of Pd(OH)$_2$ (0.011 g) in ethyl acetate at ambient temperature. The mixture was stirred under hydrogen atmosphere using pressure balloon at ambient temperature for 40 hours. The reaction mass was filtered over Celite and the solvent removed from the filtrate under high vacuum resulting in 0.010 mg of (−)-epicatechin [24].

Analytical Data:

ESIMS: 291 (M$^+$)

$^1$H-NMR (D6-DMSO, 300 MHz): δ (ppm) 9.11 (s, 1H), 8.90 (s, 1H), 8.81 (s, 1H), 8.72 (s, 1H), 6.88 (s, 1H), 6.65 (s, 2H), 5.89 (d, 1H, J=2.1 Hz), 5.70 (d, 1H, J=2.4 Hz), 4.72 (s, 1H), 4.66 (d, 1H, J=4.5 Hz), 3.98 (m, 1H), 2.63-2.71 (dd, 1H, J=4.2, 16.2) 2.44-2.49 (dd, 1H, J=3.3, 15.6).

Example 12

Synthesis of (R)-(2S,3S)-5,7-bis(benzyloxy)-2-(3',4'bis(benzyloxy)phenyl)chroman-3-yl 2-methoxy-2-phenylacetate [27]

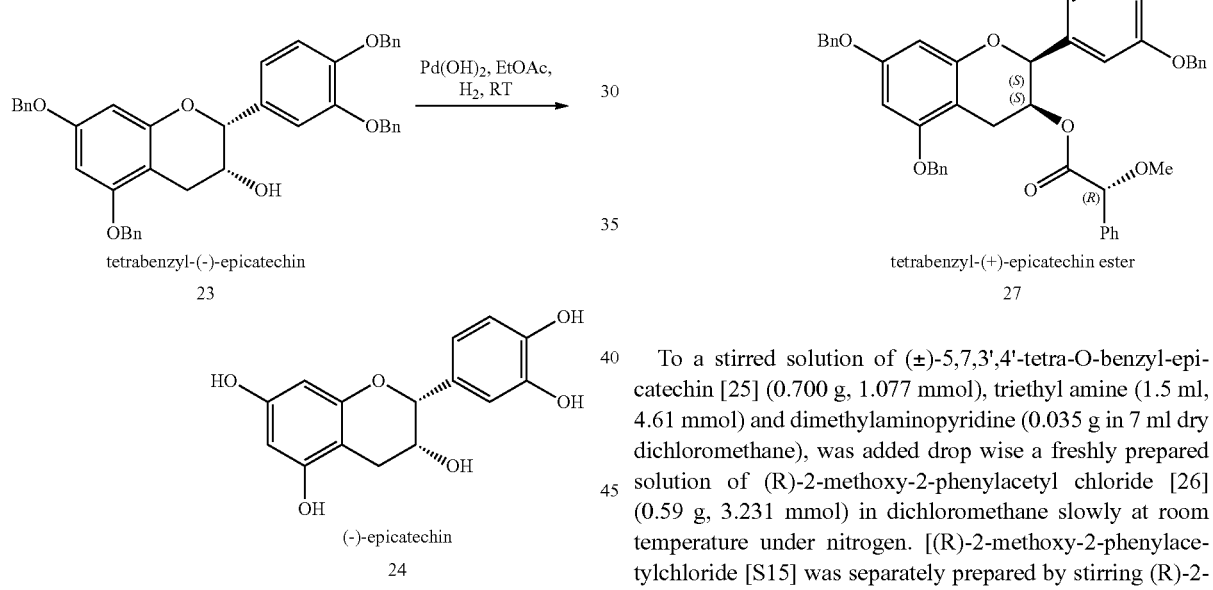

To a stirred solution of (±)-5,7,3',4'-tetra-O-benzyl-epicatechin [25] (0.700 g, 1.077 mmol), triethyl amine (1.5 ml, 4.61 mmol) and dimethylaminopyridine (0.035 g in 7 ml dry dichloromethane), was added drop wise a freshly prepared solution of (R)-2-methoxy-2-phenylacetyl chloride [26] (0.59 g, 3.231 mmol) in dichloromethane slowly at room temperature under nitrogen. [(R)-2-methoxy-2-phenylacetylchloride [S15] was separately prepared by stirring (R)-2-methoxy-2-phenylacetic acid and thionyl Chloride in dry dichloromethane with catalytic amount of dimethylformamide for 30 min. and removing the excess thionylchloride and dichloromethane by high vacuum) After the addition, the reaction mass was stirred at 40° C. for 5 to 6 hours and monitored by TLC. On complete consumption of the starting material the reaction mixture was cooled to ambient temperature and organic layer was washed with water followed by brine solution. Organic layer was dried over anhydrous sodium sulphate and concentrated under vacuum to yield thick viscous semi solid (900 mg). The viscous solid was treated with 10 mL methanol to yield solid precipitates. The Precipitates were filtered to give a solid (750 mg) which was enriched in the desired diastereoisomer [27] with a diastereomeric excess of 40% based on $^1$H NMR and HPLC analysis.

Example 13

Synthesis of 4H-chromene [15] from 2H-chromene [16]

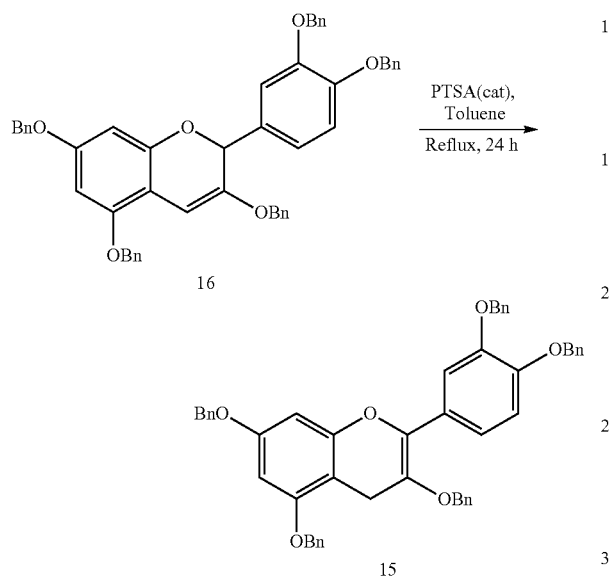

To a stirred solution of [16] (0.200 g, 0.27 mmol) in toluene (10 ml) was added para-toluene sulfonic acid (0.013 mmol) at room temperature. The reaction mixture was stirred at room temperature for 15 min then the reaction temperature was raised to 85 to 90° C. and stirred at this temperature for overnight. Reaction mixture was quenched with addition of water and diluted with ethyl acetate. The combined organic layer was washed with saturated sodium bicarbonate solution and evaporated under reduced pressure to afford dark red sticky material [15] which was used further for a conversion to epicatechin without any purification.

Example 13

Fractional Crystallization of Diastereoisomers

The 0.750 g solid was then dissolved in a minimum amount of dichloromethane followed by addition of few drops of methanol to make it turbid and left for overnight. Solid precipitates thus obtained was filtered off, dried and evaluated for diastereomeric excess using HPLC and $^1$H NMR. Four repetitions of the above precipitation process led to 50 mg of product [27] with diastereomeric excess >92%. (12% yield from racemic epicatechin).

Analytical Data:

ESIMS: 799.8 ($M^+$+1)

$^1$H-NMR (CDCl$_3$, 300 MHz): δ (ppm) 7.48-6.92 (m, 28H), 6.27-6.26 (d, 1H, J=2.1 Hz), 6.20-6.19 (d, 1H, J=2.1 Hz), 5.45 (m, 1H), 5.17 (s, 4H), 5.01-5.04 (d, s, 3H), 4.93-4.82 (dd, 2H, J=11.7, 21.6), 4.57 (s, 1H) 3.17 (s, 3H), 2.87-2.79 (dd, 1H, J=4.2, 16.2) 2.72-2.65 (dd, 1H, J=3.3, 15.6).

Example 14

Synthesis of (2S,3S)-5,7,3',4'-Tetra-O-benzyl-epicatechin [28]

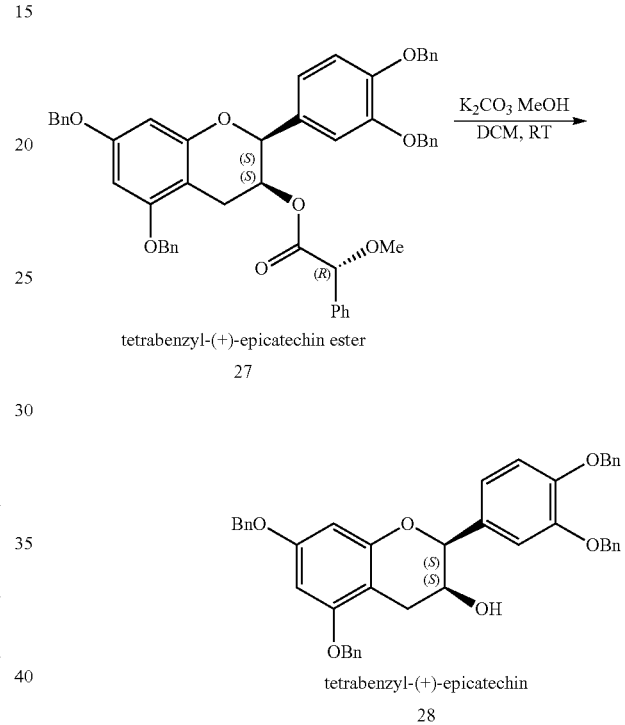

To a stirred solution of (R)-(2S,3S)-5,7-bis(benzyloxy)-2-(3',4'-bis(benzyloxy)phenyl)chroman-3-yl 2-methoxy-2-phenylacetate [27] (0.050 g, 0.063 mmol) in methanol (0.25 ml) and dichloromethane (0.5 ml) was added potassium carbonate (0.026 g, 0.188 mmol) at RT and the resulting mixture was stirred for 25 to 30 hours at ambient temperature. After completion of reaction by TLC analysis, excess of solvent was distilled off and the crude solid was dissolved in dichloromethane and washed with water followed by saturated brine solution. The organic layer was separated and the solvent was removed under high vacuum after drying over sodium sulphate to yield 0.040 g (80% pure by TLC) crude (98%) of (2S,3S)-5,7,3',4'-tetra-O-benzyl-epicatechin [28].

Analytical Data:

ESIMS: 651 ($M^+$+1)

$^1$H-NMR (CDCl$_3$, 300 MHz): δ (ppm) 7.47-7.31 (m, 20H), 7.14-7.15 (d, 1H, J=1.5 Hz), 7.00-6.99 (d, 1H, J=1.5 Hz), 6.98 (s, 1H), 6.28 (s, 1H), 6.27 (s, 1H), 5.21 (s, 2H), 5.19 (s, 2H), 5.02 (s, 2H), 5.01 (s, 2H), 4.94-4.92 (d, 1H, J=6.0), 4.22 (m, 1H), 4.06 (s, 1H), 3.08-2.98 (dd, 1H, J=2.4, 17.1) 2.96-2.89 (dd, 1H, J=4.5, 17.7).

Example 15

Synthesis of (S,S)-Epicatechin [29]

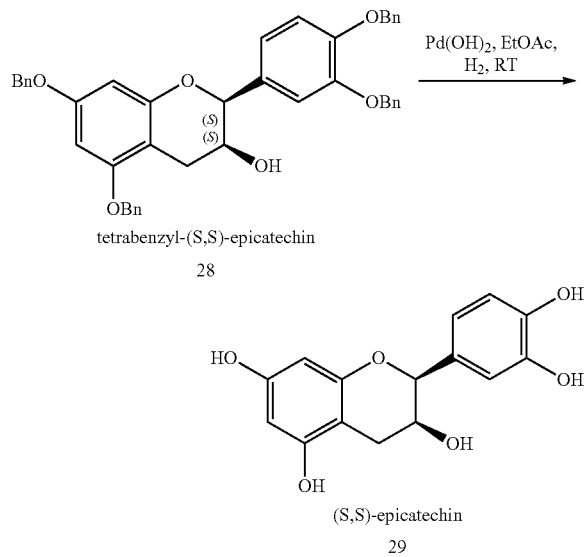

tetrabenzyl-(S,S)-epicatechin
28

(S,S)-epicatechin
29

To a stirred solution of (2S,3S)-5,7,3',4'-tetrabenzylated epicatechin [28] (0.04 g, 0.062 mmol) in ethyl acetate (5 ml), was added a slurry of Pd(OH)$_2$ (0.006 g) in ethyl acetate at ambient temperature. The mixture was stirred under hydrogen atmosphere using pressure balloon at ambient temperature for 40 hours. The reaction mass was filtered over Celite and the solvent was removed from the filtrate using high vacuum resulting in 0.006 g (33% yield) of (S,S)-epicatechin [29] which was purified by using prep TLC (Solvent System: 15% methanol in dichloromethane) to get 0.004 g (22%, 98.43% pure) desired compound [29].

Analytical Data:

ESIMS: 291 (M$^+$)

$^1$H-NMR (D6-DMSO, 300 MHz): δ (ppm) 9.11 (s, 1H), 8.90 (s, 1H), 8.81 (s, 1H), 8.72 (s, 1H), 6.88 (s, 1H), 6.65 (s, 2H), 5.89 (d, 1H, J=2.1 Hz), 5.70 (d, 1H, J=2.4 Hz), 4.72 (s, 1H), 4.66 (d, 1H, J=4.5 Hz), 3.98 (m, 1H), 2.63-2.71 (dd, 1H, J=4.2, 16.2) 2.44-2.49 (dd, 1H, J=3.3, 15.6).

Example 16

Chiral Preparative HPLC Resolution of Racemic Epicatechin/catechin

Analytical HPLC Method of Separation:

The racemic mixture of epicatechin was dissolved in methanol and checked for its chiral purity on reverse phase CHIRAL PAK® IC (250×4.6) mm, 5µ column at 25° C. temperature. The mobile phase used was hexanes/ethanol/trifluoroacetic acid//60/40/0.05 (v/v/v) with a flow rate of 1.0 ml/minute and sample injection volume of 10 µl. The signals were monitored at UV 280 nm with PDA. The both isomers separated with a retention time difference of about 1.6 minutes. The faster moving isomer on HPLC eluted at 4.7 minute while the slower moving isomer came at 6.3 minute on a 15 minute run.

Preparative HPLC Method of Separation:

The racemic mixture (0.200 g) was dissolved in methanol and separated on a preparative HPLC on CHIRAL PAK® IC (250×20) mm column at 25° C. temperature. The sample injection volume was 2.0 ml with a feed concentration of 5 mg/ml. The mobile phase used was Hexanes/EtOH//60/40 v/v with a flow rate of 18 ml/minute. The detection was done at UV 280 nm with PDA. The faster moving epicatechin isomer I (0.085 g) eluted at 4.7 minute and the slower moving epicatechin isomer II (0.084 g) at 6.3 minute with a qualitative purity of 99.6% and 99.8% respectively.

Assignment of absolute configuration to the either of the resolved isomers was done based on retention time of the two enantiomers of the racemic epicatechin synthesized compared with the retention time of the commercially available natural epicatechin (2R,3R) under similar HPLC conditions. Based on the retention time, the slow moving isomer eluted at 6.3 minutes was assigned to be (−)-epicatechin ((2R,3R)-2-(3,4-Dihydroxyphenyl)-3,4-dihydro-1 (2H)-benzopyran-3,5,7-triol)isomer and the fast moving isomer which eluted at 4.7 minutes was assigned to be (+)-epicatechin (((2S,3S)-2-(3,4-Dihydroxyphenyl)-3,4-dihydro-1(2H)-benzopyran-3,5,7-triol)isomer.

We claim:

1. A process for the preparation of compounds of Formula (I)

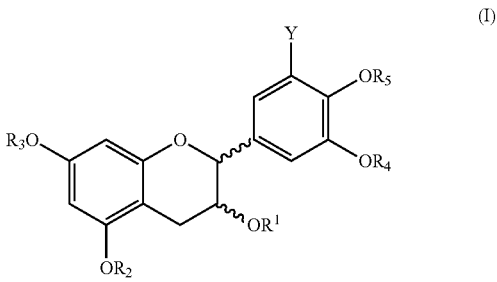

or enantiomers, diastereomers or mixtures thereof, or pharmaceutically acceptable salts thereof, wherein;

Y is selected from the group consisting of H and OR$_6$;

R$^1$, R$_2$, R$_3$, R$_4$, R$_5$ and R$_6$ are independently selected from the group consisting of H, acetyl, allyl, propargyl, benzyl, 2-fluoroethyl, 4-nitrobenzyl, 4-chlorobenzyl, 4-methoxybenzyl, 4-methoxybenzonitrile, cinnamyl, but-2-en-1-yl, 2-penten-1-yl, 1-trimethylsilyl-prop-1-yn-3-yl, 2-octyne-1-yl, 2-butyne-1-yl, 2-picolyl, 3-picolyl, 4-picolyl, quinolin-4-yl-methyl, oxiranylmethyl, fluoromethyl, nitromethyl, methoxycarbonylmethyl, methoxymethyl, 1-phenylethanone-2-yl, 2-butanone-1-yl, chloromethyl, phenyl sulfonylmethyl, 1-bromo-prop-1-en-3-yl, t-butyl, methyl, ethyl, trimethylsilyl, and t-butyldiphenylsilylethyl;

said process comprising the steps of:

i. protecting the hydroxyl groups of a compound of Formula (II) with one or more protecting groups, to give a compound of Formula (III)

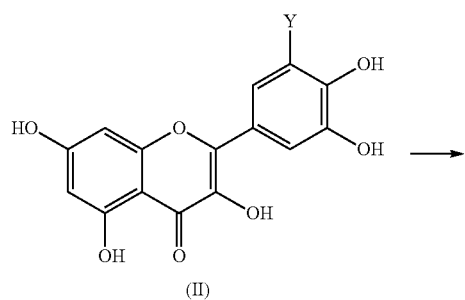

(II)

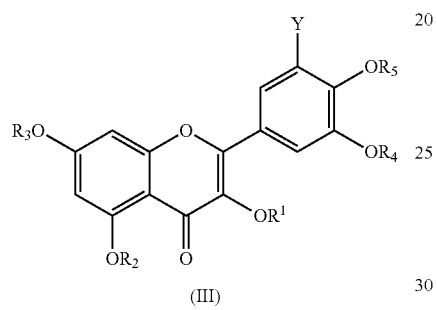

(III)

ii. treating said compound of Formula (III) with a reducing agent to produce a compound selected from the group of Formula (IV), Formula (V) and Formula (VI), wherein X is selected from halide, acetate, trifloroacetate, methanesulfonate, and hydroxyl;

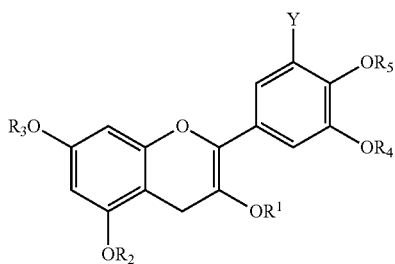

(IV)

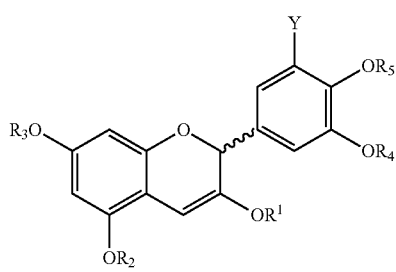

(V)

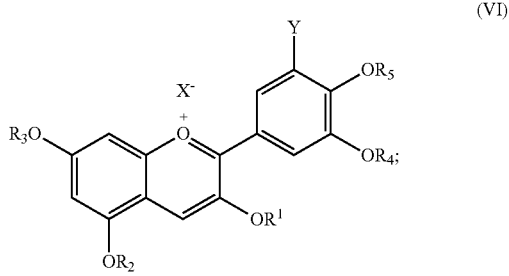

(VI)

and iii. treating a compound selected from the group of Formula (IV), Formula (V) and Formula (VI) with a reducing agent to produce a compound of Formula (I).

2. The process according to claim 1, wherein the reducing agent of step (iii) is a chiral reducing agent which produces the compound of Formula (I) as pure R,R diastereomer (Formula (VII)), pure S,S diastereomer (Formula (VIII)), or an enantiomerically enriched mixture thereof:

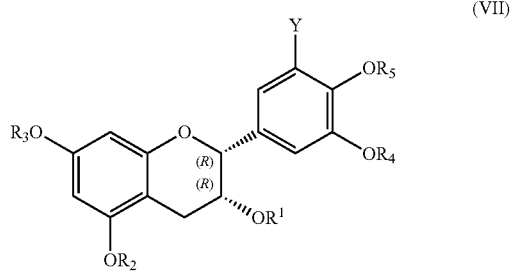

(VII)

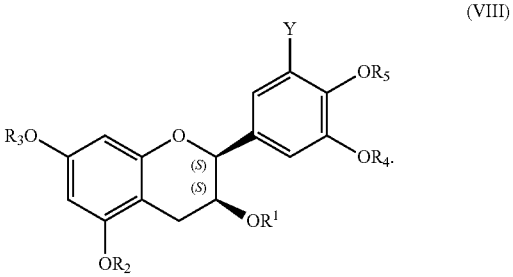

(VIII)

3. The process according to claim 1, wherein the compound of Formula (I) is selected from the group consisting of (S,S)-epicatechin, (R,R)-epicatechin, a mixture of (S,S)- and (R,R)-epicatechin, (S,S)-epigallocatechin, (R,R)-epigallocatechin and a mixture of (S,S)- and (R,R)-epigallocatechin.

4. The process according to claim 1, wherein protection of hydroxyl groups in step (i) is effected through alkylation, silylation, or esterification to form an ether, an ester, an acetate, a chloroacetate, a trifluoroacetate, a pivaloate, a benzoate, a 1,2-isopropylidene or a 1,3-isopropylidene.

5. The process according to claim 1, wherein step (i) comprises:
reacting the compound of Formula (II) with an alkylating agent selected from the group consisting of allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4-picolyl chloride, 4-bromomethylquinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone,bromochloromethane, bromomethyl phenyl sulfone and 1,3-dibromo-1-propene; wherein step (i) is optionally carried out in the presence of a base selected from the group consisting of an alkali metal hydride, a dialkylamide, a bis(trialkylsilyl)amide, an alkali metal carbonate and an alkali metal hydroxide; and optionally in an organic solvent selected from the group consisting of acetonitrile, tetrahydrofuran, dimethylacetamide, dioxane, N, N-dimethylformamide, a sulfoxide, dimethylsulfoxide and N-methylpyrrolidinone.

6. The process according to claim 5 wherein step (i) is performed in the presence of potassium carbonate in N,N-dimethylformamide at a temperature of 60° C. to 80° C., for 4 to 7 hours.

7. The process according to claim 1, wherein step (ii) comprises:
reacting the compound of Formula (III) with a reducing agent selected from the group consisting of lithium aluminium hydride, sodium borohydride, aluminium hydride, diisobutyl aluminium hydride, trialkoxy aluminium hydride, sodium amalgam, zinc mercury amalgam, and sodium bis(2-methoxyethoxy)aluminium hydride, wherein step (ii) is optionally carried out in the presence of one or more additional Lewis acids selected from the group consisting of aluminium chloride, cerium chloride, zinc chloride, boron trifluoride, and iodine, and optionally in the presence of a solvent selected from the group consisting of methyl tertiary butyl ether, tetrahydrofuran, diethyl ether, toluene and acetonitrile.

8. The process of claim 7 wherein the step (ii) is performed in methyl tertiary butyl ether or tetrahydrofuran at a temperature of from −10° C. to 80° C.

9. The process according to claim 1, wherein step (iii) is performed using hydrogen gas in the presence of a hydrogenation catalyst selected from the group consisting of platinum, palladium, ruthenium, rhodium and nickel, and/or in the presence of a solvent selected from the group consisting of methanol, ethanol, ethyl acetate, tetrahydrofuran, acetic acid and mixtures thereof.

10. The process of claim 9 wherein step (iii) is performed in the presence of palladium on carbon and a solvent selected from the group consisting of methanol, ethanol, ethyl acetate and a mixture thereof at a temperature ranging from 25° C. to 60° C. at a pressure ranging from 4 to 50 psi.

11. The process according to claim 1, further comprising converting the compound of Formula (V) to the compound of Formula (IV), in the presence of an acid catalyst selected from the group consisting of para-toluenesulfonic acid and one or more Lewis acids selected from a group consisting of aluminum chloride, cerium chloride, zinc chloride, boron trifluoride, and iodine, in the presence of a solvent selected from the group consisting of methanol, ethanol, ethyl acetate, tetrahydrofuran, methyl tertiary butyl ether, diethyl ether, toluene, acetonitrile and acetic acid.

12. The process according to claim 11 wherein converting the compound of Formula (V) to the compound of Formula (IV) is carried out in the presence of para-toluenesulfonic acid and toluene at a temperature of from 85° C. to 90° C.

13. The process according to claim 1, further comprising converting the compound of Formula (VI) to the compound of Formula (IV) in the presence of a reducing agent, wherein the reducing agent is sodium amalgam, zinc mercury amalgam, or a metal hydride selected from the group consisting of sodium bis (2-methoxyethoxy)aluminum hydride, lithium aluminum hydride, sodium borohydride, sodium cyanoborohydride, aluminum hydride, isobutyl aluminum hydride and trialkoxy aluminum hydride, optionally in the presence of a Lewis acid selected from the group consisting of aluminum chloride, cerium chloride, zinc chloride, boron trifluoride, and iodine, in the presence of one or more solvents selected from the group consisting of methanol, ethanol, acetic acid, ethyl acetate, methyl t-butyl ether, diethyl ether, toluene, acetonitrile, dichloromethane and tetrahydrofuran.

14. The process according to claim 13 wherein converting the compound of Formula (VI) to the compound of Formula (IV) is carried out in the presence of sodium cyanoborohydride, acetic acid, and dichloromethane at a temperature of 0° C. to 35° C.

15. The process according to claim 1, further comprising resolving the compound of Formula (I) into a pure stereoisomer by enzymatic resolution, chemical resolution, chiral chromatography, chiral induced fractional crystallization or partial crystallization of a diastereomeric mixture of corresponding esters generated by the functionalization of one hydroxyl group of Formula (I) with an optically pure acid.

16. The process according to claim 15, wherein the compound of Formula (I) is resolved by a method comprising one or more of the steps of:
i. protecting all but one of the hydroxyl groups of the compound of Formula (I) using one or more achiral protecting groups;
ii. coupling the unprotected hydroxyl group with an optically pure acid to form an ester as a mixture of two diastereomers;
iii. separating the two diastereomers formed in step (ii) by fractional or partial crystallization to obtain an optically pure or diastereomerically enriched ester;
iv. hydrolyzing the optically pure or diastereomerically enriched ester to obtain an enantiomerically enriched protected compound; and
v. deprotecting the enantiomerically enriched protected compound to give a compound of Formula (I).

17. The process according to claim 16, wherein the compound of Formula (I) is epicatechin and resolution comprises the steps of:
i. protecting any four of the hydroxyl groups of epicatechin;
ii. coupling the unprotected hydroxyl group with an optically pure acid to form an ester as a mixture of two diastereomers;
iii. separating the two diastereomers to provide a diastereomerically enriched ester;
iv. hydrolyzing the diastereomerically enriched ester to obtain enantiomerically enriched protected epicatechin; and
v. deprotecting the enantiomerically enriched protected epicatechin to provide epicatechin as a pure enantiomer or an enantiomerically enriched mixture.

18. The process according to claim 17, wherein the compound of Formula (I) is (R,R) epicatechin, (S,S) epicatechin or a mixture thereof.

19. A compound of Formula (IV) or Formula (V)

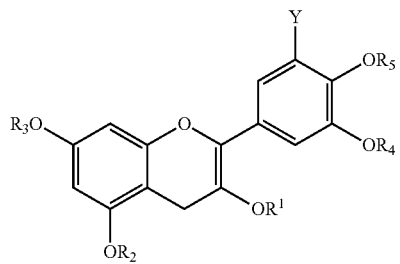
(IV)

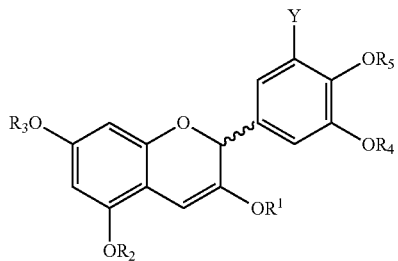
(V)

wherein:
Y is selected from the group consisting of H and $OR_6R^1$, $R_2$, $R_3$, $R_4$, $R_5$, and $R_6$ are independently selected from the group consisting of H, benzyl, acetyl, $Si(CH_3)_3$, and allyl, provided that at least one of $R^1$, $R_2$, $R_3$, $R_4$, $R_5$ and $R_6$ is benzyl.

20. The compound of claim 19, wherein each of $R^1$, $R_2$, $R_3$, $R_4$, $R_5$, and $R_6$ is benzyl.

* * * * *